US012797314B2

(12) United States Patent
Hara et al.

(10) Patent No.: US 12,797,314 B2
(45) Date of Patent: Nov. 17, 2026

(54) COMPOSITION FOR KERATIN FIBERS

(71) Applicant: L'Oreal, Paris (FR)

(72) Inventors: Takuya Hara, Kawasaki (JP); Leila Hercouet, Saint-Ouen (FR); Akihiro Kasai, Kawasaki (JP); Shuchismita Basu, Kawasaki (JP); Hidetoshi Yamada, Kawasaki (JP)

(73) Assignee: L'Oreal, Paris (FR)

( * ) Notice: Subject to any disclaimer, the term of this patent is extended or adjusted under 35 U.S.C. 154(b) by 354 days.

(21) Appl. No.: 18/251,240

(22) PCT Filed: Oct. 29, 2021

(86) PCT No.: PCT/JP2021/040901
§ 371 (c)(1),
(2) Date: Apr. 30, 2023

(87) PCT Pub. No.: WO2022/097742
PCT Pub. Date: May 12, 2022

(65) Prior Publication Data

US 2023/0404872 A1 Dec. 21, 2023

(30) Foreign Application Priority Data

Nov. 6, 2020 (JP) ................................ 2020-185823
Dec. 7, 2020 (FR) ...................................... 2012757

(51) Int. Cl.

| | |
|---|---|
| ***A61Q 5/10*** | (2006.01) |
| ***A61K 8/02*** | (2006.01) |
| ***A61K 8/19*** | (2006.01) |
| ***A61K 8/25*** | (2006.01) |
| ***A61K 8/41*** | (2006.01) |
| ***A61K 8/44*** | (2006.01) |
| ***A61K 8/49*** | (2006.01) |
| ***A61Q 5/06*** | (2006.01) |
| ***A61Q 5/08*** | (2006.01) |

(52) U.S. Cl.
CPC .............. *A61K 8/25* (2013.01); *A61K 8/0291* (2013.01); *A61K 8/19* (2013.01); *A61K 8/41* (2013.01); *A61K 8/44* (2013.01); *A61K 8/4913* (2013.01); *A61K 8/492* (2013.01); *A61Q 5/08* (2013.01); *A61K 2800/43* (2013.01)

(58) Field of Classification Search
CPC . A61Q 5/00; A61Q 5/08; A61Q 5/065; A61Q 5/10; A61Q 5/06; A61K 2800/10; A61K 2800/43; A61K 2800/4324; A61K 8/41; A61K 2800/882; A61K 2800/4322; A61K 8/25
See application file for complete search history.

(56) References Cited

U.S. PATENT DOCUMENTS

| | | | |
|---|---|---|---|
| 4,003,699 | A | 1/1977 | Rose et al. |
| RE30,199 | E | 1/1980 | Rose et al. |
| 5,046,516 | A | 9/1991 | Barradas |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,663,366 | A | 9/1997 | Neunhoeffer et al. |
| 5,708,151 | A | 1/1998 | Möckli |
| 5,766,576 | A | 6/1998 | Löwe et al. |
| 5,957,140 | A | 9/1999 | McGee |
| 6,099,592 | A | 8/2000 | Vidal et al. |
| 6,284,003 | B1 | 9/2001 | Rose et al. |
| 6,730,789 | B1 | 5/2004 | Birault et al. |
| 7,135,167 | B2 | 11/2006 | Legrand et al. |
| 8,257,447 | B2 | 9/2012 | Legrand et al. |
| 8,343,237 | B2 | 1/2013 | Legrand et al. |
| 10,449,134 | B2 | 10/2019 | Voisin et al. |
| 10,772,819 | B2 | 9/2020 | Baghdadli et al. |
| 11,083,681 | B2 | 8/2021 | Mukai et al. |
| 11,389,387 | B2 | 7/2022 | Haake et al. |
| 11,497,707 | B2 | 11/2022 | Viscogliosi et al. |
| 11,612,554 | B2 | 3/2023 | Botto et al. |
| 12,029,810 | B2 | 7/2024 | Viscogliosi et al. |
| 12,239,726 | B2 | 3/2025 | Agach et al. |
| 2005/0251928 | A1 | 11/2005 | Kravchenko et al. |
| 2009/0071494 | A1 | 3/2009 | Nguyen et al. |
| 2011/0138545 | A1 | 6/2011 | Legrand et al. |

(Continued)

FOREIGN PATENT DOCUMENTS

| | | | |
|---|---|---|---|
| CN | 103505379 | A | 1/2014 |
| CN | 104684533 | A | 6/2015 |

(Continued)

OTHER PUBLICATIONS

Database Mintel GNPD, "Hair Colorant Cream Palette," Schwarzkopf & Henkel, ID#: 6569409, 2019 [retrieved Nov. 20, 2024], 6 pages.
Office Action in JP2020185823, mailed Nov. 25, 2024, 27 pages.
International Search Report for counterpart Application No. PCT/JP2021/040901, dated Mar. 9, 2022.
Mintel: "Hair Bleaching Agent," Schwarzkopf & Henkel, Record No. 8158129, XP055837001, Oct. 5, 2020.
Mintel: "Bleach Blonde Permanent Hair Lightening Kit," Clairol, Record ID 10231227, XP055840345, Sep. 9, 2005.
International Search Report and Written Opinion for counterpart Application No. PCT/EP2021/068034, dated Aug. 27, 2021.
International Search Report and Written Opinion for counterpart Application No. PCT/EP2021/068032, dated Aug. 27, 2021.

(Continued)

*Primary Examiner* — Tracy Liu
(74) *Attorney, Agent, or Firm* — The Marbury Law Group, PLLC

(57) ABSTRACT

The present invention relates to a composition for keratin fibers, comprising: (a) at least one inorganic compound selected from silicic acids and salts thereof; (b) at least one organic compound selected from amino acids, derivatives thereof, and salts thereof; (c) at least one alkaline agent other than the (a) inorganic compound and the (b) organic compound; (d) at least one fatty material; and (e) water. The composition according to the present invention can be used for oxidative dyeing or bleaching of keratin fibers such as hair.

9 Claims, 1 Drawing Sheet

(56) References Cited

U.S. PATENT DOCUMENTS

| | | | | |
|---|---|---|---|---|
| 2013/0156716 | A1 | 6/2013 | Yontz | |
| 2015/0265525 | A1* | 9/2015 | Benn | A61Q 5/10 206/568 |
| 2015/0297481 | A1 | 10/2015 | Wahler et al. | |
| 2016/0136068 | A1 | 5/2016 | Mignon et al. | |
| 2016/0136069 | A1 | 5/2016 | Hercouet et al. | |
| 2018/0042831 | A1 | 2/2018 | Voisin et al. | |
| 2018/0064617 | A1* | 3/2018 | Lee | A61K 8/0291 |
| 2018/0116930 | A1 | 5/2018 | Degeorge et al. | |
| 2018/0116942 | A1 | 5/2018 | Mahadeshwar et al. | |
| 2018/0153780 | A1* | 6/2018 | Azizova | A61Q 5/10 |
| 2019/0184209 | A1 | 6/2019 | Schroeder et al. | |
| 2020/0163867 | A1 | 5/2020 | Viscoglioshi et al. | |
| 2023/0165771 | A1 | 6/2023 | Hercouet et al. | |
| 2023/0172826 | A1 | 6/2023 | Agach et al. | |
| 2023/0233431 | A1 | 7/2023 | Thomas et al. | |
| 2023/0381080 | A1 | 11/2023 | Sengmany et al. | |

FOREIGN PATENT DOCUMENTS

| | | | |
|---|---|---|---|
| CN | 105307727 | A | 2/2016 |
| CN | 111148500 | A | 5/2020 |
| DE | 2359399 | A1 | 6/1975 |
| DE | 3843892 | A1 | 6/1990 |
| DE | 4133957 | A1 | 4/1993 |
| DE | 19543988 | A1 | 5/1997 |
| DE | 102009027360 | A1 | 1/2011 |
| DE | 102017223063 | A1 | 6/2019 |
| EP | 0714954 | A2 | 6/1996 |
| EP | 0770375 | A1 | 5/1997 |
| EP | 2356978 | A2 | 8/2011 |
| FR | 2733749 | A1 | 11/1996 |
| FR | 2801308 | A1 | 5/2001 |
| FR | 2814948 | A1 | 4/2002 |
| FR | 2870119 | A1 | 11/2005 |
| FR | 2886136 | A1 | 12/2006 |
| FR | 2922444 | A1 | 4/2009 |
| FR | 2925305 | A1 | 6/2009 |
| FR | 2925317 | A1 | 6/2009 |
| FR | 3021529 | A1 | 12/2015 |
| GB | 1026978 | A | 4/1966 |
| GB | 1153196 | A | 5/1969 |
| JP | 02-019576 | A | 1/1990 |
| JP | 05-163124 | A | 6/1993 |
| JP | H11139941 | A | 5/1999 |
| JP | 2002114653 | A | 4/2000 |
| JP | 2000169343 | A | 6/2000 |
| JP | 2009-107959 | A | 5/2009 |
| JP | 2009102259 | A | 5/2009 |
| JP | 2009263239 | A | 11/2009 |
| JP | 2015506906 | A | 3/2015 |
| JP | 2015129095 | A | 7/2015 |
| JP | 2016525077 | A | 8/2016 |
| JP | 2018500347 | A | 1/2018 |
| KR | 10-2007-0118489 | A | 12/2007 |
| KR | 10-2020-0051526 | A | 5/2020 |
| WO | 94/08969 | A1 | 4/1994 |
| WO | 94/08970 | A1 | 4/1994 |
| WO | 95/01772 | A1 | 1/1995 |
| WO | 95/15144 | A1 | 6/1995 |
| WO | 96/15765 | A1 | 5/1996 |
| WO | 2009/050295 | A2 | 4/2009 |
| WO | 2009/080670 | A2 | 7/2009 |
| WO | 2011000648 | A2 | 1/2011 |
| WO | 2014053504 | A2 | 4/2014 |
| WO | 2015093264 | A1 | 6/2015 |
| WO | 2016102543 | A1 | 6/2016 |
| WO | 2016154692 | A1 | 10/2016 |
| WO | 2017189574 | A1 | 11/2017 |
| WO | 2018/068947 | A2 | 4/2018 |
| WO | 2019/012219 | A1 | 1/2019 |
| WO | 2019/234193 | A1 | 12/2019 |
| WO | 2022/003038 | A1 | 1/2022 |
| WO | 2022003040 | A1 | 1/2022 |

OTHER PUBLICATIONS

Todd et al., "Volatile Silicone Fluids for Cosmetics," Cosmetics and Toiletries, vol. 91, Jan. 76, pp. 27-32.
Mintel: "Treatment," Kose Cosmeport Je L'Aime Amino Supreme Satin Sleek, Record No. 7462129, XP055784739, Mar. 1, 2020.
Mintel: "Conditioner," Kose Japan Stephen Knoll Premium Sleek Shine Repair Silky Smooth, Kose Japan, Record No. 3489415, XP055784742, Sep. 1, 2015.
Mintel: "Infinite Strength Shampoo," Saint-Algue —SAF, Record No. 5012531, XP055784745, Aug. 1, 2017.
Mintel: "Treatment Mask," Kose Cosmeport Japan, Record ID 5412235, XP055784752, Jan. 1, 2018.
Translation of Notice of Reasons for Refusal for counterpart JP Application No. 2022-574260, dated Jan. 15, 2024.
Translation of Notice of Reasons for Refusal for counterpart JP Application No. 2022-574815, issued Dec. 4, 2023.
Non-Final Office Action for copending U.S. Appl. No. 18/013,659, dated Jul. 18, 2024.
Non-Final Office Action for copending U.S. Appl. No. 18/013,657, dated May 15, 2025.
International Search Report and Written Opinion for counterpart PCT/EP2021/068033, dated Aug. 27, 2021.
Office Action and Search Report in CN202180045353.1, including English translation mailed Nov. 13, 2024, 14 pages.
Restriction Requirement for copending U.S. Appl. No. 18/008,259, dated Apr. 3, 2024.
Non-Final Office Action for copending U.S. Appl. No. 18/008,259, dated May 19, 2025.
Final Office Action for copending U.S. Appl. No. 18/008,259, dated Aug. 28, 2025.
Indian Office Action for counterpart Application No. 202317030605, including English translation, dated Oct. 31, 2025.
Final Office Action for copending U.S. Appl. No. 18/013,657, dated Nov. 10, 2025.
Notice of Allowance for copending U.S. Appl. No. 18/013,659, dated Nov. 6, 2024.
International Search Report and Written Opinion for counterpart Application No. PCT/EP2021/084188, dated Feb. 14, 2022.
English Translation of Chinese Office Action for counterpart Application No. 202180074983.1, dated Dec. 11, 2024.
Non-Final Office Action for copending U.S. Appl. No. 18/265,749, dated Jun. 23, 2025.
Final Office Action for copending U.S. Appl. No. 18/265,749, dated Dec. 4, 2025.
The State Intellectual Property Office of People's Republic of China, "The First Office Action," issued in counterpart Chinese Patent Application No. 202180044997.9, including English translation, dated Apr. 28, 2025 (15 pages).

* cited by examiner

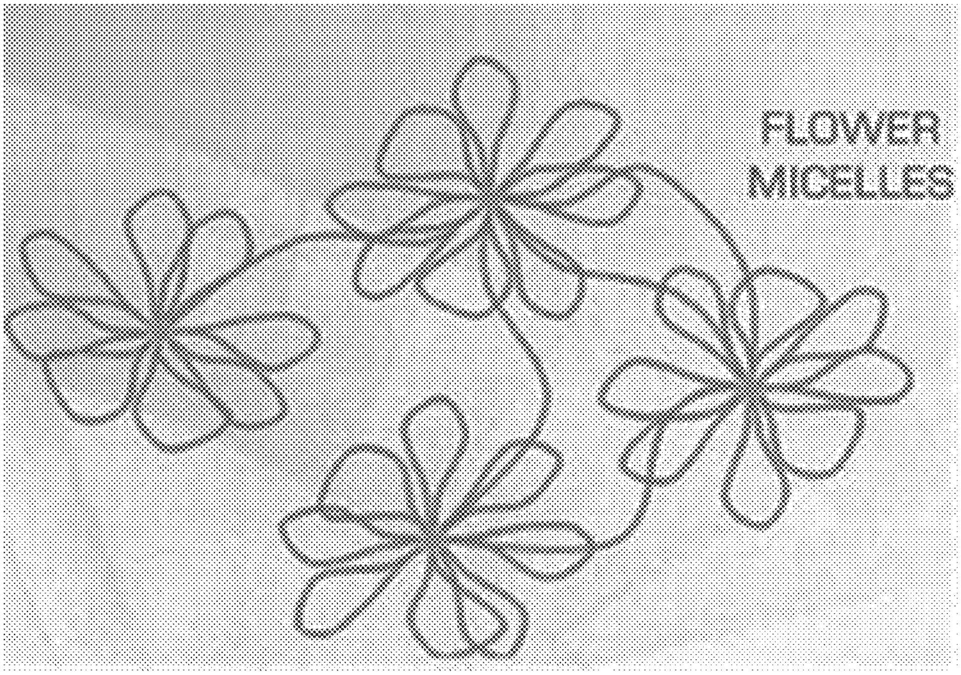
FLOWER
MICELLES

COMPOSITION FOR KERATIN FIBERS

CROSS REFERENCE TO RELATED APPLICATIONS

This is a National Stage Application of PCT/JP2021/040901, filed internationally on Oct. 29, 2021, which claims priority to Japanese Application No. JP 2020-185823, filed Nov. 6, 2020, and French Application No. FR 2012757, filed Dec. 7, 2020, the contents of all of which are incorporated by reference herein in their entireties.

TECHNICAL FIELD

The present invention relates to a composition for keratin fibers, in particular, a composition for bleaching or dyeing keratin fibers such as hair.

BACKGROUND ART

It is known to dye keratin fibers, in particular hair, using dyeing compositions containing oxidative coloring precursors, generally called oxidative bases, such as ortho- or para-phenylenediamines, ortho- or para-aminophenols and heterocyclic compounds. These oxidative bases are generally combined with couplers. These oxidative bases and couplers are colorless or weakly colored compounds. However, when combined with oxidizing agents, they can provide colored dye molecules through an oxidative condensation process.

This type of coloring by oxidation, i.e., oxidative dyeing, makes it possible to get colors with very high visibility, coverage of white hair, and a wide variety of shades. Oxidative dyeing is widely used because of the high color uptake as compared with direct dyeing using so-called direct dyes.

In order to perform oxidative dyeing, typically, a composition comprising oxidative base(s), as well as coupler(s), with alkaline agent(s), is mixed with a developer composition comprising oxidizing agent(s) to prepare a ready-to-use composition, and then, the ready-to-use composition is applied onto keratin fibers.

The developer composition is capable of bleaching keratin fibers due to the function of the oxidizing agent(s) in the composition. Therefore, the developer composition as well as the ready-to-use composition (this may not include any oxidation base with or without any coupler) may be used to bleach keratin fibers.

DISCLOSURE OF INVENTION

It is preferable that the above-described compositions can provide good bleaching or dyeing effects.

On the other hand, bleaching or dyeing keratin fibers with the above-described compositions tend to damage the keratin fibers because they comprise alkaline agent(s).

Thus, there is a need for a composition which can bleach or dye keratin fibers such as hair, wherein the composition can provide good bleaching or dyeing effects while it can reduce the damage of the keratin fibers.

Thus, an objective of the present invention is to provide a composition for keratin fibers, in particular for bleaching or oxidative dyeing of keratin fibers, which can provide the keratin fibers with good bleaching or dyeing effects, while it can reduce the damage of the keratin fibers.

The above objective can be achieved by a composition for keratin fibers, comprising:

(a) at least one inorganic compound selected from silicic acids and salts thereof;

(b) at least one organic compound selected from amino acids, derivatives thereof, and salts thereof;

(c) at least one alkaline agent other than the (a) inorganic compound and the (b) organic compound;

(d) at least one fatty material; and (e) water.

The (a) inorganic compound may be selected from silicates, preferably metasilicates, and more preferably alkali metal metasilicates.

The amount of the (a) inorganic compound(s) in the composition according to the present invention may be from 0.05% to 10% by weight, preferably from 0.1% to 5% by weight, and more preferably from 0.5% to 2% by weight, relative to the total weight of the composition.

The (b) organic compound may be selected from amino acids, preferably cyclic α-amino acids, and more preferably, non-aromatic cyclic α-amino acids, and salts thereof.

The amino acids may have an isoelectric point of less than 7.

The (b) organic compound may be selected from glycine, alanine, valine, leucine, isoleucine, serine, threonine, cysteine, methionine, aspartic acid, asparagine, glutamic acid, phenylalanine, tyrosine, tryptophan and proline.

The amount of the (b) organic compound(s) in the composition according to the present invention may be from 0.1% to 10% by weight, preferably from 0.5% to 5% by weight, and more preferably from 1% to 3% by weight, relative to the total weight of the composition.

The (c) alkaline agent may be selected from ammonia, alkanolamines, derivatives thereof, and salts thereof.

The alkanolamine may be selected from the group consisting of monoethanolamine, diethanolamine, triethanolamine, monoisopropanolamine, diisopropanolamine, N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof.

The amount of the (c) alkaline agent(s) in the composition according to the present invention may be from 0.1% to 20% by weight, preferably from 0.5% to 15% by weight, and more preferably from 1% to 10% by weight, relative to the total weight of the composition.

The (d) fatty material may be selected from hydrocarbon oils, preferably aliphatic hydrocarbon oils, and more preferably mineral oils.

The amount of the (d) fatty material(s) in the composition according to the present invention may be from 40% by weight or more, preferably 45% by weight or more, and more preferably 50% by weight or more, relative to the total weight of the composition.

The amount of the (e) water in the composition according to the present invention may be from 10% to 40% by weight, preferably from 15% to 35% by weight, and more preferably from 20% to 30% by weight, relative to the total weight of the composition.

The composition according to the present invention may further comprise (f) at least one dye.

The present invention also relates to a process for keratin fibers comprising the steps of:

(1) mixing a first composition and a second composition to prepare a mixture, wherein the first composition comprises (a) at least one inorganic compound selected from silicic acids and salts thereof, (b) at least one organic compound selected from amino acids, derivatives thereof, and salts thereof,
(c) at least one alkaline agent other than the (a) inorganic compound and the (b) organic compound,
(d) at least one fatty material,
(e) water, and optionally (f) at least one dye, and
the second composition comprises
(g) at least one oxidizing agent; and
(2) applying the mixture to the keratin fibers.

BRIEF DESCRIPTION OF DRAWINGS

FIG. 1 shows a front view of an example of a network formed by an associative polyurethane thickener in water in which the hydrophobic parts of the associative polyurethane thickener connect to form quasi-micelles which are indicated as flower micelles.

BEST MODE FOR CARRYING OUT THE INVENTION

After diligent research, the inventors have discovered that it is possible to provide a composition for keratin fibers, in particular for bleaching or oxidative dyeing of keratin fibers, which can provide the keratin fibers with good bleaching or dyeing effects, while it can reduce the damage of the keratin fibers.

Thus, the composition according to the present invention comprises:
(a) at least one inorganic compound selected from silicic acids and salts thereof;
(b) at least one organic compound selected from amino acids, derivatives thereof, and salts thereof;
(c) at least one alkaline agent other than the (a) inorganic compound and the (b) organic compound;
(d) at least one fatty material; and
(e) water.

The composition according to the present invention can be used as a cosmetic composition for keratin fibers such as hair, preferably a cosmetic composition for bleaching or oxidative dyeing of keratin fibers.

Further, the composition according to the present invention can provide keratin fibers with good bleaching or dyeing effects.

Furthermore, the composition according to the present invention can reduce the damage of keratin fibers.

In addition, the present invention can reduce odor if ammonia is not used as the alkaline agent. In general, ammonia is used as an alkaline agent. However, ammonia can cause a strong odor. Therefore, it is also possible for the present invention to prevent or reduce the odor, if ammonia is not used as the alkaline agent.

The present invention also relates to a process for keratin fibers comprising the steps of:
(1) mixing a first composition and a second composition to prepare a mixture, wherein
the first composition comprises
(a) at least one inorganic compound selected from silicic acids and salts thereof,
(b) at least one organic compound selected from amino acids, derivatives thereof, and salts thereof,
(c) at least one alkaline agent other than the (a) inorganic compound and the (b) organic compound,
(d) at least one fatty material,
(e) water, and optionally (f) at least one dye, and
the second composition comprises
(g) at least one oxidizing agent; and
(2) applying the mixture to the keratin fibers.

Hereafter, the composition and process according to the present invention will be described in a detailed manner.

[Composition]

(Inorganic Compound)

The composition according to the present invention comprises (a) at least one inorganic compound selected from silicic acids and salts thereof (hereafter, may be referred to as (a) inorganic compound). If two or more (a) inorganic compounds are used, they may be the same or different.

Silicic acid is a compound which can be represented by the chemical formula: $[SiO_x(OH)_{4-2x}]_n$ wherein x denotes an integer of from 0 to 2, preferably 0 or 1, and more preferably 1, and n denotes an integer of 1 to 4, preferably an integer of 1 or 2, and more preferably 1.

For example, silicic acid may be selected from the group consisting of orthosilicic acid ($H_4SiO_4$), metasilicic acid ($H_2SiO_3$), metadisilicic acid ($H_2Si_2O_5$) and a mixture thereof.

Salts of silicic acid are referred to as silicates. The silicates may be selected from the group consisting of orthosilicates, metasilicates, metadisilicates and a mixture thereof. It is preferable that the silicates be metal salts or ammonium salts. It is more preferable that the silicates be selected from the group consisting of alkali metal salts, alkali earth metal salts and ammonium salts.

It is preferable that the (a) inorganic compound be selected from silicates, more preferably metasilicates, and even more preferably alkali metal metasilicates.

It is preferable that the (a) inorganic compound be water-soluble. The term "water-soluble" here means that the solubility in water at 20° C. under atmospheric pressure is 10 g/l or more, more preferably 30 g/l or more, and even more preferably 50 g/l or more. It is preferable that the solubility of the (a) inorganic compound in water at 20° C. under atmospheric pressure be 100 g/l or more, preferably 150 g/l or more, and more preferably 200 g/l or more.

It is preferable that the pH of an aqueous solution of the (a) inorganic compound be more than 12, more preferably 11 or more, and even more preferably 12 or more.

Thus, it is preferable that the (a) inorganic compound be selected from water-soluble silicates, more preferably water-soluble metasilicates, and even more preferably water-soluble alkali metal metasilicates.

It is preferable that the (a) inorganic compound not encompass water-insoluble silicic acids and salts thereof, in particular silica or silicon dioxide.

It is preferable that the (a) inorganic compound be selected from sodium metasilicate, potassium metasilicate, and a mixture thereof.

It is more preferable that the (a) inorganic compound be sodium metabisilicate. Sodium metabisilicate ($Na_2SiO_3$) is an anhydrous compound, but can also exist in its hydrated forms (with 5 or 9 molecules of water).

The amount of the (a) inorganic compound(s) in the composition according to the present invention is 0.05% by weight or more, preferably 0.1% by weight or more, and more preferably 0.5% by weight or more, relative to the total weight of the composition.

On the other hand, the amount of the (a) inorganic compound(s) in the composition according to the present invention may be 10% by weight or less, preferably 5% by weight or less, and more preferably 2% by weight or less, relative to the total weight of the composition.

The amount of the (a) inorganic compound(s) in the composition according to the present invention may be from 0.05% to 10% by weight, preferably from 0.1% to 5% by weight, and more preferably from 0.5% to 2% by weight, relative to the total weight of the composition.

(Organic Compound)

The composition according to the present invention comprises (b) at least one organic compound selected from amino acids, derivatives thereof, and salts thereof (hereafter, may be referred to as (b) organic compound). If two or more (b) organic compounds are used, they may be the same or different.

In one embodiment, the (b) organic compound is selected from amino acids.

The amino acid has at least one amino group and at least one carboxyl group.

The amino group may be a primary amino group, a secondary amino group or a tertiary amino group, preferably a primary amino group or a secondary amino group, and more preferably a secondary amino group.

It is preferable that the molecular weight of the amino acid be less than 1000, more preferably less than 500, and even more preferably less than 200. Thus, it is preferable that the amino acid not be a polymer. In other words, it is preferable that the amino acid be a non-polymeric amino acid.

The amino acid may be selected from acidic amino acids, basic amino acids and neutral amino acids. The acidic amino acids typically have one amino group and two carboxyl groups. The basic amino acids typically have two amino groups and one carboxyl group. The number of amino group(s) and the number of carboxyl group(s) in the neutral amino groups are the same.

The amino acid may be in the D- or L-form.

The amino acid may be hydrophilic or hydrophobic. A hydrophilic amino acid is preferable.

The amino acid may be selected from α-amino acids, β-amino acids, γ-amino acids and δ-amino acids.

It is preferable that the amino acid be selected from an α-amino acid in which an amino group is bonded to the carbon atom to which a carboxyl group is bonded.

The α-amino acid may be selected from non-cyclic α-amino acids and cyclic α-amino acids.

The non-cyclic α-amino acid may be selected from the group consisting of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

The cyclic α-amino acid may be selected from non-aromatic cyclic α-amino acids such as pyrrolidone carboxylic acid (pyroglutamic acid or pidolic acid). Pyrrolidone carboxylic acid can be formed by intramolecular condensation with the amino group and the carboxyl group of glutamic acid.

It is preferable that the amino acids have an isoelectric point of less than 7, preferably less than 6.5, and more preferably 6 or less. Thus, it is preferable that the amino acids be selected from neutral amino acids and acidic amino acids. In other words, it is preferable that the amino acids not be basic amino acids such as arginine, histidine and lysine.

In one embodiment, the (b) organic compound is selected from the derivatives of amino acids.

The derivatives of amino acids (amino acid derivatives) may be selected from amino acids in which the hydrogen atom on the nitrogen atom of the amino group in the amino acids is substituted with at least one substituent.

As the substituent, mention may be made of, for example, an alkyl group, acyl group, an alkenyl group, an alkoxyl group and an alkoxycarbonyl group.

The alkyl group may be a linear, branched or cyclic alkyl group. The alkyl group may be a linear or branched $C_1$-$C_6$ alkyl group, preferably a $C_1$-$C_4$ alkyl group, such as a methyl group, an ethyl group, a propyl group, an i-propyl group and a butyl group. On the other hand, the alkyl group may be a cyclic $C_3$-$C_6$ alkyl group, such as a cyclopentyl group and a cyclohexyl group.

The acyl group may be a $C_1$-$C_6$ acyl group such as a formyl group and an acetyl group.

The alkenyl group may be a $C_2$-$C_6$ alkenyl group such as a vinyl group, an allyl group, a butylene group, a pentenyl group and a hexenyl group.

The alkoxy group may be a $C_1$-$C_6$ alkoxy group such as a methoxy group, an ethoxy group and a propoxy group.

The alkoxycarbonyl group may be a $C_1$-$C_6$ alkoxycarbonyl group such as a methoxycarbonyl group, an ethoxycarbonyl group, and a propoxycarbonyl group.

The above substituent may be further substituted with at least one group such as a halogen atom, an amino group, a nitro group, a cyano group, a hydroxyl group and an aromatic group such as a phenyl group.

In one embodiment, the (b) organic compound is selected from the salts of amino acids or the salts of amino acid derivatives.

The type of the salts of amino acids or the salts of amino acid derivatives is not limited. The salts may be acid salts or basic salts. As acid salts, mention may be made of, for example, inorganic acid salts such as hydrochloride, sulfates, nitrates, and phosphates, and organic acid salts such as citrates, oxalates, acetates, formates, maleates, and tartrates. As basic salts, mention may be made of, for example, inorganic base salts such as sodium salt, potassium salt, calcium salt, magnesium salt, copper salt, zinc salt, aluminum salt and ammonium salts, and organic base salts such as triethylammonium salts, triethanolammonium salts, pyridinium salts and diisopropyl ammonium salts. Sodium salt is preferable.

It is preferable that the (b) organic compound be selected from glycine, alanine, valine, leucine, isoleucine, serine, threonine, cysteine, methionine, aspartic acid, asparagine, glutamic acid, phenylalanine, tyrosine, tryptophan and proline.

The amount of the (b) organic compound(s) in the composition according to the present invention is 0.1% by weight or more, preferably 0.5% by weight or more, and more preferably 1% by weight or more, relative to the total weight of the composition.

On the other hand, the amount of the (b) organic compound(s) in the composition according to the present invention may be 10% by weight or less, preferably 5% by weight or less, and more preferably 3% by weight or less, relative to the total weight of the composition.

The amount of the (b) organic compound(s) in the composition according to the present invention may be from 0.1% to 10% by weight, preferably from 0.5% to 5% by weight, and more preferably from 1% to 3% by weight, relative to the total weight of the composition.

(Alkaline Agent)

The composition according to the present invention comprises (c) at least one alkaline agent other than the (a) inorganic compound and the (b) organic compound (hereafter, may be referred to as (c) alkaline agent). If two or more (c) alkaline agents are used, they may be the same or different.

The (c) alkaline agent is different from the (a) inorganic compound or the (b) organic compound.

The (c) alkaline agent may be selected from ammonia, alkanolamines, derivatives of alkanolamines (alkanolamine derivatives), and salts of alkanolamines or alkanolamine derivatives.

The alkanolamines have an alkane structure with at least one hydroxyl group and at least one amino group.

As the alkanolamines, mention may be made of, for example, mono-, di-, and tri-ethanolamines. The alkanolamine may be selected from the group consisting of monoethanolamine, diethanolamine, triethanolamine, monoisopropanolamine, diisopropanolamine, N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris (hydroxymethylamino)methane, and a mixture thereof.

The alkanolamine derivative may be selected from alkanolamines in which the hydrogen atom on the nitrogen atom, if present, of the amino group in the alkanolamines is substituted with at least one substituent.

As the substituent, mention may be made of, for example, an alkyl group, an alkenyl group, and an alkynyl group.

The alkyl group may be a linear, branched or cyclic alkyl group. The alkyl group may be a linear or branched $C_1$-$C_6$ alkyl group, preferably a $C_1$-$C_4$ alkyl group, such as a methyl group, an ethyl group, a propyl group, an i-propyl group and a butyl group. On the other hand, the alkyl group may be a cyclic $C_3$-$C_6$ alkyl group, such as a cyclopentyl group and a cyclohexyl group.

The alkenyl group may be a $C_2$-$C_6$ alkenyl group such as a vinyl group, an allyl group, a butylene group, a pentenyl group and a hexenyl group.

The alkynyl group may be a $C_2$-$C_6$ alkynyl group such as an ethynyl group, and a propanyl group.

The above substituent may be further substituted with at least one group such as a halogen atom, a nitro group, a cyano group, a hydroxyl group and an aromatic group such as a phenyl group.

The type of the salts of alkanolamines and alkanolamine derivatives is not limited. The salts may be acid salts. As acid salts, mention may be made of, for example, inorganic acid salts such as hydrochloride, sulfates, nitrates, and phosphates, and organic acid salts such as citrates, oxalates, acetates, formates, maleates, and tartrates.

The amount of the (c) alkaline agent(s) in the composition according to the present invention may be from 0.1% by weight or more, preferably 0.5% by weight or more, and more preferably from 1% by weight or more, relative to the total weight of the composition.

The amount of the (c) alkaline agent(s) in the composition according to the present invention may be from 20% by weight or less, preferably from 15% by weight or less, and more preferably from 10% by weight or less, relative to the total weight of the composition.

The amount of the (c) alkaline agent(s) in the composition according to the present invention may be from 0.1% to 20% by weight, preferably from 0.5% to 15% by weight, and more preferably from 1% to 10% by weight, relative to the total weight of the composition.

(Fatty Material)

The composition according to the present invention comprises (d) at least one fatty material. Two or more fatty materials may be used in combination. Thus, a single type of fatty material or a combination of different types of fatty material may be used.

The term "fatty material" means an organic compound that is insoluble in water at ordinary temperature (25° C.) and at atmospheric pressure (760 mmHg) (solubility of less than 5%, preferably 1% and even more preferentially 0.1%). The fatty material may contain, in its structure, a sequence of at least two siloxane groups or at least one hydrocarbon-based chain containing at least 6 carbon atoms. In addition, the fatty substances may be soluble in organic solvents under the same temperature and pressure conditions, for instance chloroform, ethanol, benzene or decamethylcyclopentasiloxane.

In the scope of the present invention, it has to be noted that the fatty material does not comprise any $C_2$-$C_3$ oxyalkylene units or any glycerolated units.

The (d) fatty material may be in the form of a liquid or a solid. Here, "liquid" and "solid" mean that the fatty material is in the form of a liquid or a paste (non-solid) or solid, respectively, at ambient temperature (25° C.) under atmospheric pressure (760 mmHg or $10^5$ Pa). It is preferable that the (d) fatty material comprise at least one fatty material in the form of a liquid or a paste, preferably in the form of a liquid, at ambient temperature and under atmospheric pressure. The (d) fatty material in the form of a liquid at ambient temperature under atmospheric pressure can be referred to as "oil". It is preferable that the (d) fatty material be selected from oils.

If the (d) fatty material is selected from oils, the composition according to the present invention can have an oil phase or oil phases.

The (d) fatty material may be selected from polar oils, non-polar oils, and mixtures thereof. It is preferable that the (d) fatty material be selected from non-polar oils.

The (d) fatty material may be selected from the group consisting of oils of animal or plant origin, mineral oils, synthetic glycerides, esters of fatty alcohols and/or fatty acids other than animal or plant oils and synthetic glycerides, fatty alcohols, fatty acids, silicone oils and hydrocarbons. These fatty materials may be volatile or non-volatile. Preferably, the (d) fatty material is selected from the group consisting of oils of animal or plant origin, synthetic glycerides, fatty esters other than animal or plant oils and synthetic glycerides, fatty alcohols, fatty acids, silicone oils, and hydrocarbons. More preferably, the (d) fatty material is selected from silicones and hydrocarbons, preferably aliphatic hydrocarbons, and more preferably mineral oils, and mixtures thereof.

As examples of aliphatic hydrocarbons, mention may be made of, for example, linear or branched hydrocarbons such as mineral oil (e.g., liquid paraffin), paraffin, vaseline or petrolatum, naphthalenes, and the like; hydrogenated polyisobutene, isoeicosan, polydecenes, hydrogenated polyisobutenes such as Parleam, and decene/butene copolymer; and mixtures thereof.

As examples of other aliphatic hydrocarbons, mention may also be made of linear or branched, or possibly cyclic $C_6$-$C_{16}$ lower alkanes. Examples that may be mentioned include hexane, undecane, dodecane, tridecane and isoparaffins such as isohexadecane and isodecane.

As examples of synthetic glycerides, mention may be made of, for instance, caprylic/capric acid triglycerides, for instance those sold by the company, Stéarineries Dubois or those sold under the names Miglyol® 810, 812 and 818 by the company, Dynamit Nobel.

As examples of silicone oils, mention may be made of, for example, linear organopolysiloxanes such as dimethylpolysiloxanes or dimethicones, methylphenylpolysiloxanes, methylhydrogenpolysiloxanes, and the like; cyclic organopolysiloxanes such as octamethylcyclotetrasiloxane, decamethylcyclopentasiloxane, dodecamethylcyclohexasiloxane, and the like; and mixtures thereof.

As examples of plant oils, mention may be made of, for example, linseed oil, *camellia* oil, macadamia nut oil, sunflower oil, apricot oil, soybean oil, arara oil, hazelnut oil, corn oil, mink oil, olive oil, avocado oil, sasanqua oil, castor oil, safflower oil, jojoba oil, sunflower oil, almond oil, grapeseed oil, sesame oil, soybean oil, peanut oil, and mixtures thereof.

As examples of animal oils, mention may be made of, for example, squalene, perhydrosqualene and squalane.

As examples of the esters of a fatty acid and/or of a fatty alcohol, which are advantageously different from the animal or plant oils as well as the synthetic glycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, esters of $C_4$-$C_{22}$ dicarboxylic or tricarboxylic acids and of $C_1$-$C_{22}$ alcohols and esters of mono-, di- or tricarboxylic acids and of $C_2$-$C_{26}$ di-, tri-, tetra- or pentahydroxy alcohols may also be used.

The following may especially be mentioned: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, it is preferable to use ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate or cetyl octanoate.

The composition may also comprise, as the fatty ester, sugar esters and diesters of $C_6$-$C_{30}$ and preferably $C_{12}$-$C_{22}$ fatty acids. The term "sugar" means oxygen-bearing hydrocarbon-based compounds containing several alcohol functions, with or without aldehyde or ketone functions, and which contain at least 4 carbon atoms. These sugars may be monosaccharides, oligosaccharides or polysaccharides.

Examples of suitable sugars that may be mentioned include sucrose (or saccharose), glucose, galactose, ribose, fructose, maltose, mannose, arabinose, xylose and lactose, and derivatives thereof, especially alkyl derivatives, such as methyl derivatives, for instance methylglucose.

The sugar esters of fatty acids may be selected especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise one to three conjugated or non-conjugated carbon-carbon double bonds.

The esters according to this variant may also be selected from mono-, di-, tri-, tetraesters and polyesters, and mixtures thereof.

These esters may be selected, for example, from oleates, laurates, palmitates, myristates, behenates, cocoates, stearates, linoleates, linolenates, caprates and arachidonates, or mixtures thereof such as, especially, oleo-palmitate, oleo-stearate and palmito-stearate mixed esters.

It is more particularly preferable to use monoesters and diesters and especially sucrose, glucose or methylglucose mono- or dioleates, stearates, behenates, oleopalmitates, linoleates, linolenates and oleostearates.

An example that may be mentioned is the product sold under the name Glucate® DO, which is a methylglucose dioleate, by the company Amerchol.

Examples of esters or mixtures of esters of sugar and of fatty acid that may also be mentioned include:

- the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
- the products sold under the name Ryoto Sugar Esters, for example referred to as B370 and corresponding to sucrose behenate formed from 20% monoester and 80% di-triester-polyester;
- the sucrose mono-dipalmito-stearate sold by the company Goldschmidt under the name Tegosoft® PSE.

The fatty material may be at least one fatty acid, and two or more fatty acids may be used. The fatty acids should be in acidic form (i.e., unsalified, to avoid soaps) and may be saturated or unsaturated and contain from 6 to 30 carbon atoms and in particular from 9 to 30 carbon atoms, which are optionally substituted, in particular with one or more hydroxyl groups (in particular 1 to 4). If they are unsaturated, these compounds may comprise one to three conjugated or non-conjugated carbon-carbon double bonds. They are more particularly selected from myristic acid, palmitic acid, stearic acid, behenic acid, oleic acid, linoleic acid, linolenic acid and isostearic acid. Preferably the fatty material is not a fatty acid.

The fatty material may be at least one fatty alcohol, and two or more fatty alcohols may be used.

The term "fatty alcohol" here means any saturated or unsaturated, linear or branched $C_8$-$C_{30}$ fatty alcohol, which is optionally substituted, in particular with one or more hydroxyl groups (in particular 1 to 4). If they are unsaturated, these compounds may comprise one to three conjugated or non-conjugated carbon-carbon double bonds.

Among the $C_8$-$C_{30}$ fatty alcohols, $C_{12}$-$C_{22}$ fatty alcohols, for example, are used. Mention may be made among these of lauryl alcohol, cetyl alcohol, stearyl alcohol, isostearyl alcohol, oleyl alcohol, behenyl alcohol, linoleyl alcohol, undecylenyl alcohol, palmitoleyl alcohol, linolenyl alcohol, myristyl alcohol, arachidonyl alcohol and erucyl alcohol, and mixtures thereof. In one embodiment, cetyl alcohol, stearyl alcohol or a mixture thereof (e.g., cetearyl alcohol), as well as myristyl alcohol, can be used as a solid fatty material. In another embodiment, isostearyl alcohol can be used as a liquid fatty material.

The fatty material may be a wax. Here, "wax" means that the fatty material is substantially in the form of a solid at room temperature (25° C.) under atmospheric pressure (760 mmHg), and has a melting point generally of 35° C. or more. As the waxy fatty material, waxes generally used in cosmetics can be used alone or in combinations thereof.

For example, the wax may be selected from carnauba wax, microcrystalline waxes, ozokerites, hydrogenated jojoba oil, polyethylene waxes such as the wax sold under the name "Performalene 400 Polyethylene" by the company New Phase Technologies, silicone waxes, for instance poly ($C_{24}$-$C_{28}$)alkylmethyldimethylsiloxane, such as the product sold under the name "Abil Wax 9810" by the company Goldschmidt, palm butter, the $C_{20}$-$C_{40}$ alkyl stearate sold under the name "Kester Wax K82H" by the company Kester Keunen, stearyl benzoate, shellac wax, and mixtures thereof. For example, a wax selected from carnauba wax, candelilla wax, ozokerites, hydrogenated jojoba oil and polyethylene waxes can be used. In at least one embodiment, the wax is preferably selected from candelilla wax and ozokerite, and mixtures thereof.

It is preferable that the (d) fatty material be selected from hydrocarbon oils, preferably aliphatic hydrocarbon oils, and more preferably mineral oils.

The amount of the (d) fatty material(s) in the composition according to the present invention may be 10% by weight or more, preferably 20% by weight or more, more preferably 30% by weight or more, relative to the total weight of the composition.

Furthermore, the amount of the (d) fatty material(s) in the composition according to the present invention may be 40% by weight or more, preferably 45% by weight or more, and even more preferably 50% by weight or more, relative to the total weight of the composition.

The amount of the (d) fatty material(s) in the composition according to the present invention may be 80% by weight or less, preferably 75% by weight or less, and more preferably 70% by weight or less, relative to the total weight of the composition.

The amount of the (d) fatty material(s) in the composition according to the present invention may range from 40% to 80% by weight, preferably from 45% to 75% by weight, and more preferably from 50% to 70% by weight, relative to the total weight of the composition.

(Water)

The composition according to the present invention comprises (e) water.

The (e) water can form an aqueous phase of the composition according to the present invention while the (d) fatty material may form an oil phase.

If the composition according to the present invention is in the form of a W/O or O/W emulsion, the aqueous phase of the composition according to the present invention can be dispersed or inner phases in the W/O emulsion or a continuous or outer phase in the O/W emulsion.

The amount of the (e) water in the composition according to the present invention may be 10% by weight or more, preferably 15% by weight or more, and more preferably 20% by weight or more, relative to the total weight of the composition.

On the other hand, the amount of the (e) water in the composition according to the present invention may be 40% by weight or less, preferably 35% by weight or less, and more preferably 30% by weight or less, relative to the total weight of the composition.

The amount of the (e) water may be from 10% to 40% by weight, preferably from 15% to 35% by weight, and more preferably from 20% to 30% by weight, relative to the total weight of the composition.

The pH of the composition according to the present invention may be more than 7, preferably 7.5 or more, and more preferably 8 or more. Thus, the composition according to the present invention is alkaline. It is preferable that the pH of the composition according to the present invention be 13 or less, more preferably 12 or less, and even more preferably 11 or less.

The pH may be adjusted to the desired value using the (c) alkaline agent(s) and/or at least one acidifying agent.

The acidifying agents can be, for example, mineral or organic acids, for instance hydrochloric acid, phosphoric acid, carboxylic acids, for instance tartaric acid, citric acid, and lactic acid, or sulphonic acids, or ascorbic acid.

The acidifying agent may be present in an amount ranging from less than 1% by weight, preferably from 0.5% by weight or less, and more preferably 0.3% by weight or less, relative to the total weight of the composition.

(Dye)

The composition according to the present invention may comprise (f) at least one dye. If two or more (f) dyes are used, they may be the same or different.

It is preferable that the dye be selected from oxidative dyes.

The oxidative dyes may be selected from oxidation bases and couplers.

The oxidation base can be selected from those conventionally known in oxidation dyeing, preferably from the group consisting of ortho- and para-phenylenediamines, double bases, ortho- and para-aminophenols, heterocyclic bases, and the acid addition salts thereof.

There may be mentioned in particular:

(I) the para-phenylenediamines of the following formula (I) and their addition salts with an acid:

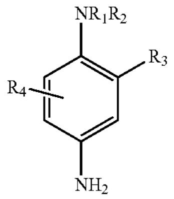

(I)

in which:

$R_1$ represents a hydrogen atom, a $C_1$-$C_4$ alkyl radical, a monohydroxy($C_1$-$C_4$ alkyl) radical, a polyhydroxy-($C_2$-$C_4$ alkyl) radical, a ($C_1$-$C_4$)alkoxy($C_1$-$C_4$)alkyl radical, a $C_1$-$C_4$ alkyl radical substituted with a nitrogen-containing group, a phenyl radical, or a 4'-aminophenyl radical;

$R_2$ represents a hydrogen atom, a $C_1$-$C_4$ alkyl radical, a monohydroxy($C_1$-$C_4$ alkyl) radical, a polyhydroxy($C_2$-$C_4$ alkyl) radical, a ($C_1$-$C_4$)alkoxy($C_1$-$C_4$)alkyl radical, or a $C_1$-$C_4$ alkyl radical substituted with a nitrogen-containing group;

$R_1$ and $R_2$ may also form with the nitrogen atom carrying them a 5- or 6-membered nitrogen-containing heterocycle optionally substituted with one or more alkyl, hydroxyl, or ureido groups;

$R_3$ represents a hydrogen atom, a halogen atom such as a chlorine atom, a $C_1$-$C_4$ alkyl radical, a sulpho radical, a carboxyl radical, a monohydroxy($C_1$-$C_4$ alkyl) radical, a hydroxy($C_1$-$C_4$ alkoxy) radical, an acetylamino ($C_1$-$C_4$ alkoxy) radical, a mesylamino($C_1$-$C_4$ alkoxy) radical, or a carbamoylamino($C_1$-$C_4$ alkoxy) radical; and $R_4$ represents a hydrogen or halogen atom or a $C_1$-$C_4$ alkyl radical.

Among the nitrogen-containing groups of formula (I) above, there may be mentioned in particular the amino, mono($C_1$-$C_4$)alkylamino, ($C_1$-$C_4$)dialkylamino, ($C_1$-$C_4$)trialkylamino, monohydroxy($C_1$-$C_4$)alkylamino, di(monohydroxy($C_1$-$C_4$)alkyl)amino, imidazolinium, and ammonium radicals.

Among the para-phenylenediamines of formula (I) above, mention may be more particularly made of para-phenylenediamine, para-tolylenediamine, 2-chloro-paraphenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethylpara-phenylenediamine, N,N-diethyl-para-phenylenediamine, N,N-dipropyl-paraphenylenediamine, 4-amino-N,N-diethyl-3-methylaniline, N,N-bis(β-hydroxyethyl)-paraphenylenediamine, 4-N,N-bis(β-hydroxyethyl) amino-2-methylaniline, 4-N,N-bis(β-hydroxyethyl)amino-2-chloroaniline, 2-β-hydroxyethyl-para-phenylenediamine, 2-fluoro-paraphenylenediamine, 2-isopropyl-para-phenylenediamine, N-(β-hydroxypropyl)-paraphenylenediamine, 2-hydroxymethyl-para-phenylenediamine, N,N-dimethyl-3-methylpara-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylamino-ethyloxy-para-phenylenediamine, N-((3-methoxyethyl)-para-phenylenediamine, 2-methyl-1-N-β-hydroxyethyl-para-phenylenediamine, N-(4-aminophenyl)-3-hydroxypyrrolidine, 2-[{2-[(4-aminophenyl)amino]ethyl}(2-hydroxyethyl)amino]-ethanol, and their addition salts with an acid.

Among the para-phenylenediamines of formula (I) above, most particularly preferred are para-phenylenediamine, para-tolylenediamine, 2-isopropyl-paraphenylenediamine, 2-β-hydroxyethyl-para-phenylenediamine, 2β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, and their addition salts with an acid.

(II) According to the present invention, "double bases" are understood to mean compounds containing at least two aromatic rings on which amino and/or hydroxyl groups are carried.

Among the double bases which can be used as oxidation bases in the dyeing compositions in accordance with the present invention, mention may be made in particular of compounds corresponding to the following formula (II), and their addition salts with an acid:

(II)

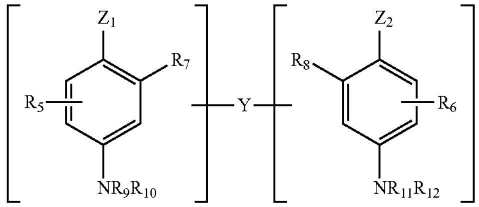

in which:

$Z_1$ and $Z_2$, which are identical or different, represent a hydroxyl or —$NH_2$ radical which may be substituted with a $C_1$-$C_4$ alkyl radical or with a linking arm Y;

the linking arm Y represents a linear or branched alkylene chain comprising from 1 to 14 carbon atoms, which may be interrupted by or which may end with one or more nitrogen-containing groups and/or one or more heteroatoms such as oxygen, sulphur, or nitrogen atoms, and optionally substituted with one or more hydroxyl or $C_1$-$C_6$ alkoxy radicals;

$R_5$ and $R_6$ represent a hydrogen or halogen atom, a $C_1$-$C_4$ alkyl radical, a monohydroxy($C_1$-$C_4$ alkyl) radical, a polyhydroxy($C_2$-$C_4$ alkyl) radical, an amino($C_1$-$C_4$ alkyl) radical, or a linking arm Y;

$R_7$, $R_8$, $R_9$, $R_{10}$, $R_{11}$ and $R_{12}$, which are identical or different, represent a hydrogen atom, a linking arm Y, or a $C_1$-$C_4$ alkyl radical; it being understood that the compounds of formula (II) contain only one linking arm Y per molecule.

Among the nitrogen-containing groups of formula (II) above, mention may be made in particular of the amino, mono($C_1$-$C_4$)alkylamino, ($C_1$-$C_4$)dialkylamino, ($C_1$-$C_4$)trialkylamino, monohydroxy($C_1$-$C_4$)alkylamino, imidazolinium, and ammonium radicals.

Among the double bases of formulae (II) above, mention may be more particularly made of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl) tetramethylenediamine, N,N'-bis(4-methylaminophenyl) tetramethylenediamine, N,N'-bis(ethyl)-N,N'-bis(4'-amino-3'-methylphenyl)ethylene-diamine, 1,8-bis(2,5-diaminophenoxy)-3,5-dioxaoctane, and their addition salts with an acid.

Among these double bases of formula (II), N,N'-bis(β-hydroxyethyl)-N,N'-bis(4'-aminophenyl)-1,3-diaminopropanol, 1,8-bis(2,5-diaminophenoxy)-3,5-dioxaoctane, or one of their addition salts with an acid are particularly preferred.

(III) The para-aminophenols corresponding to the following formula (III), and their addition salts with an acid:

(III)

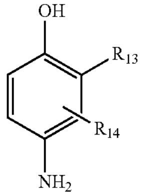

in which:

$R_{13}$ represents a hydrogen atom, or a halogen atom such as fluorine, a $C_1$-$C_4$ alkyl, monohydroxy($C_1$-$C_4$ alkyl), ($C_1$-$C_4$)alkoxy($C_1$-$C_4$)-alkyl, amino($C_1$-$C_4$ alkyl), or hydroxy($C_1$-$C_4$)alkylamino-($C_1$-$C_4$ alkyl) radical, $R_{14}$ represents a hydrogen atom, or a halogen atom such as fluorine, a $C_1$-$C_4$ alkyl, monohydroxy($C_1$-$C_4$ alkyl), polyhydroxy($C_2$-$C_4$ alkyl), amino($C_1$-$C_4$ alkyl), cyano ($C_1$-$C_4$ alkyl), or ($C_1$-$C_4$)alkoxy($C_1$-$C_4$)alkyl radical.

Among the para-aminophenols of formula (III) above, mention may be more particularly made of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, and their addition salts with an acid.

(IV) The ortho-aminophenols which can be used as oxidation bases in the context of the present invention are chosen in particular from 2-aminophenol, 2-amino-1-hydroxy-5-methylbenzene, 2-amino-1-hydroxy-6-methylbenzene, 5-acetamido-2-aminophenol, and their addition salts with an acid.

(V) Among the heterocyclic bases which can be used as oxidation bases in the dyeing compositions in accordance with the present invention, mention may be more particularly made of pyridine derivatives, pyrimidine derivatives, pyrazole derivatives, and their addition salts with an acid.

Among the pyridine derivatives, mention may be more particularly made of the compounds described for example in patents GB 1,026,978 and GB 1,153,196, such as 2,5-diaminopyridine, 2-(4-methoxyphenyl)amino-3-aminopyridine, 2,3-diamino-6-methoxypyridine, 2-(β-methoxyethyl) amino-3-amino-6-methoxypyridine, 3,4-diaminopyridine, and their addition salts with an acid.

Among the pyrimidine derivatives, mention may be more particularly made of the compounds described, for example, in patents DE 2 359 399; JP 88-169571; and JP 91-10659, or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triamino-pyrimidine, and the pyrazolopyrimidine derivatives such as those mentioned in patent application FR-A-2 750 048 and among which there may be mentioned pyrazolo[1,5-a]-pyrimidine-3,7-diamine; 2,5-dimethyl-pyrazolo[1,5-a]-pyrimidine-3,7-diamine; pyrazolo [1,5-a]pyrimidine-3,5-diamine; 2,7-dimethylpyrazolo[1,5-a]pyrimidine-3,5-diamine; 3-aminopyrazolo[1,5-a] pyrimidin-7-ol; 3-amino-pyrazolo[1,5-a]pyrimidin-5-ol; 2-(3-amino-pyrazolo-[1,5-a]pyrimidin-7-ylamino)ethanol, 2-(7-aminopyrazolo[1,5-a]pyrimidin-3-ylamino)ethanol, 2-[(3-amino-pyrazolo[1,5-a]pyrimidin-7-yl)-(2-hydroxyethyl)amino]-ethanol, 2-[(7-aminopyrazolo[1,5-a]-pyrimidin-3-yl)-(2-hydroxyethyl)amino]ethanol, 5,6-dimethylpyrazolo-[1,5-a]pyrimidine-3,7-diamine, 2,6-dimethylpyrazolo-[1,5-a]pyrimidine-3,7-diamine, 2,5,N7,N7-tetramethyl-pyrazolo[1,5-a]pyrimidine-3,7-diamine, 3-amino-5-methyl-7-imidazolylpropyl-aminopyrazolo[1,5-a]-pyrimidine, their addition salts and their tautomeric forms, when a tautomeric equilibrium exists, and their addition salts with an acid.

Among the pyrazole derivatives, mention may more particularly be made of the compounds described in patents DE 3 843 892 and DE 4 133 957 and patent applications WO 94/08969, WO 94/08970, FR-A-2 733 749, and DE 195 43 988 such as 4,5-diamino-1-methylpyrazole, 3,4-diaminopyrazole, 4,5-diamino-1-(4'-chlorobenzyl)-pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazino-pyrazole, 1-benzyl-4,5-diamino-3-methyl-pyrazole, 4,5-diamino-3-tert-butyl-1-methylpyrazole, 4,5-diamino-1-tertbutyl-3-methylpyrazole, 4,5-diamino-1-(β-hydroxyethyl)-3-methylpyrazole, 4,5-diamino-1-β-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxy-methylpyrazole, 4,5-diamino-3-hydroxymethyl-1-methylpyrazole, 4,5-diamino-3-hydroxymethyl-1-isopropyl-pyrazole, 4,5-diamino-3-methyl-1-isopropyl-pyrazole, 4-amino-5-(2'-aminoethyl)amino-1,3-dimethylpyrazole, 3,4,5-triaminopyrazole, 1-methyl-3,4,5-triamino-pyrazole, 3,5-diamino-1-methyl-4-methylaminopyrazole, 3,5-diamino-4-(β-hydroxy-ethyl)amino-1-methylpyrazole, and their addition salts with an acid.

Among the heterocyclic bases which can be used as oxidation bases, mention may more particularly be made of diaminopyrazolopyrazolones and especially 2,3-diamino-6,7-dihydro-1H5H-[pyrazolo1,2,a]pyrazol-1-one and the addition salts of these diaminopyrazolopyrazolones with an acid.

The coupler may be an oxidation coupler which can be selected from those conventionally known in oxidation dyeing, preferably from the group consisting of meta-phenylenediamines, meta-aminophenols, meta-diphenols, naphthols, heterocyclic couplers, and the acid addition salts thereof.

The heterocyclic couplers may be selected from the group consisting of indole derivatives, indoline derivatives, sesamol and its derivatives, pyridine derivatives, pyrazolotriazole derivatives, pyrazolones, indazoles, benzimidazoles, benzothiazoles, benzoxazoles, 1,3-benzodioxoles, quinolines, and their addition salts with an acid.

These couplers are more particularly chosen from 2,4-diamino-1-(β-hydroxyethyloxy)benzene, 2-methyl-5-aminophenol, 5-N-(β-hydroxyethyl)amino-2-methylphenol, 3-aminophenol, 2-chloro-3-amino-6-methylphenol, 1,3-dihydroxybenzene, 1,3-dihydroxy-2-methylbenzene, 4-chloro-1,3-dihydroxybenzene, 2-amino-4-(β-hydroxyethylamino)-1-methoxybenzene, 1,3-diaminobenzene, 2-methyl-5-hydroxyethylaminophenol, 4-amino-2-hydroxytoluene, 1,3-bis(2,4-diaminophenoxy)-propane, sesamol, 1-amino-2-methoxy-4,5-methylene-dioxybenzene, α-naphthol, 6-hydroxyindole, 4-hydroxyindole, 4-hydroxy-N-methylindole, 6-hydroxy-indoline, 2,6-dihydroxy-4-methylpyridine, 1-H-3-methylpyrazol-5-one, 1-phenyl-3-methylpyrazol-5-one, 2-amino-3-hydroxypyridine, 3,6-dimethyl-pyrazolo[3,2-c]-1,2,4-triazole, 2,6-dimethylpyrazolo[1,5-b]-1,2,4-triazole, and their addition salts with an acid.

In general, the addition acid salts of the oxidation bases and couplers are chosen in particular from hydrochlorides, hydrobromides, sulfates, citrates, succinates, tartrates, lactates, tosylates, benzenesulfonates, phosphates, and acetates.

The amount of the (f) dye(s) in the composition according to the present invention may be 0.1% by weight or more, preferably 0.5% by weight or more, and more preferably 1% by weight or more, relative to the total weight of the composition.

On the other hand, the amount of the (f) dye(s) in the composition according to the present invention may be 15% by weight or less, preferably 10% by weight or less, and more preferably 5% by weight or less, relative to the total weight of the composition.

The amount of the (f) dye(s) in the composition according to the present invention may be from 0.1% to 15% by weight, preferably from 0.5% to 10% by weight, and more preferably from 1% to 5% by weight, relative to the total weight of the composition.

(Cationic Polymer)

The composition according to the present invention may comprise at least one cationic polymer. A single type of cationic polymer may be used, but two or more different types of cationic polymers may be used in combination.

It should be noted that, for the purposes of the present invention, the term "cationic polymer" denotes any polymer containing cationic groups and/or groups that may be ionized into cationic groups.

Such polymers may be chosen from those already known per se as improving the cosmetic properties of the hair, i.e., especially those described in patent application EP-A-337 354 and in French patents FR-2 270 846, 2 383 660, 2 598 611, 2 470 596 and 2 519 863.

The cationic polymers that are preferred are chosen from those containing units comprising primary, secondary, tertiary and/or quaternary amine groups, which may either form part of the main polymer chain or may be borne by a side substituent directly attached thereto.

The cationic polymers used generally have a number-average molecular mass of between approximately 500 and approximately $5\times10^6$ and preferably between approximately $10^3$ and approximately $3\times10^6$.

Among the cationic polymers that may be mentioned, more particularly are polymers of the polyamine, polyamino amide and polyquaternary ammonium type.

These are known products. They are described in particular in French patents 2 505 348 and 2 542 997. Among the said polymers, mention may be made of the following.

(1) homopolymers or copolymers derived from acrylic or methacrylic esters or amides and comprising at least one of the units of formula (I), (II), (III) or (IV) below:

(I)

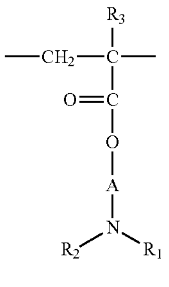

(II)

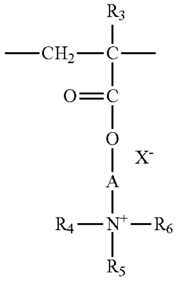

-continued (III)

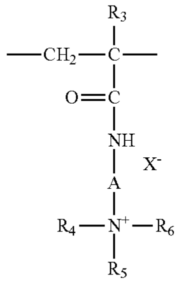

(IV)

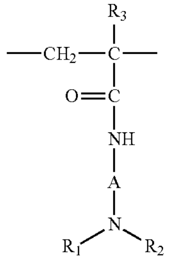

in which $R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical and preferably an alkyl group containing from 1 to 6 carbon atoms;

$R_1$ and $R_2$, which may be identical or different, represent hydrogen or an alkyl group containing from 1 to 6 carbon atoms, and preferably methyl or ethyl; and X denotes an anion derived from an inorganic or organic acid, such as a methosulfate anion or a halide such as chloride or bromide.

The polymers of family (1) can also contain one or more units derived from comonomers which may be chosen from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinyl-caprolactam, and vinyl esters.

Thus, among these polymers of family (1), mention may be made of:

- copolymers of acrylamide and of dimethylaminoethyl methacrylate quaternized with dimethyl sulfate or with a dimethyl halide, such as the product sold under the name Hercofloc by the company Hercules,
- the copolymers of acrylamide and of methacryloyloxyethyltrimethylammonium chloride described, for example, in patent application EP-A-080 976 and sold under the name Bina Quat P 100 by the company BASF,
- the copolymers of acrylamide and of methacryloyloxyethyltrimethylammonium methosulfate sold under the name Reten by the company Hercules,
- quaternized or non-quaternized vinylpyrrolidone/dialkylaminoalkyl acrylate or methacrylate copolymers, such as the products sold under the name "Gafquat" by the company ISP, for instance "Gafquat 734" or "Gafquat 755", or alternatively the products known as "Copolymer 845, 958 and 937". These polymers are described in detail in French patents 2 077 143 and 2 393 573, dimethylaminoethyl methacrylate/vinylcaprolactam/vinylpyrrolidone terpolymers, such as the product sold under the name Gaffix VC 713 by the company ISP, and vinylpyrrolidone/methacrylamidopropyldimethylamine copolymers sold in particular under the name Styleze CC 10 by ISP, and quaternized vinylpyrrolidone/dimethylaminopropyl methacrylamide copolymers such as the product sold under the name "Gafquat HS 100" by the company ISP.

(2) The cellulose ether derivatives comprising quaternary ammonium groups, which are described in French patent 1 492 597, and in particular the polymers sold under the names "JR" (JR 400, JR 125, JR 30M) or "LR" (LR 400, LR 30M) by the company Amerchol. These polymers are also defined in the CTFA dictionary as hydroxyethylcellulose quaternary ammoniums that have reacted with an epoxide substituted with a trimethylammonium group.

(3) Cationic cellulose derivatives such as the copolymers of cellulose or cellulose derivatives grafted with a water-soluble quaternary ammonium monomer, described especially in U.S. Pat. No. 4,131,576, such as hydroxyalkylcelluloses, for instance hydroxymethyl-, hydroxyethyl- or hydroxypropylcelluloses grafted especially with a methacryloylethyl-trimethylammonium, methacrylamidopropyltrimethylammonium or dimethyldiallylammonium salt.

The commercial products corresponding to this definition are more particularly the products sold under the name Celquat L 200 and Celquat H 100 by the company Akzo Nobel.

(4) The cationic guar gums described more particularly in U.S. Pat. Nos. 3,589,578 and 4,031,307, such as guar gums containing trialkylammonium cationic groups. Use is made, for example, of guar gums modified with a salt (e.g., chloride) of 2,3-epoxypropyltrimethylammonium. Mention may be made of guar hydroxypropyltrimonium chloride and hydroxypropyl guar hydroxypropyl trimonium chloride, such as those sold especially under the trade names Jaguar C13S, Jaguar C14S, Jaguar C17 and Jaguar C162 by the company Solvay.

(5) Polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are described, in particular, in French patents 2 162 025 and 2 280 361.

(6) Water-soluble polyamino amides prepared in particular by polycondensation of an acidic compound with a polyamine; these polyamino amides can be crosslinked with an epihalohydrin, a diepoxide, a dianhydride, an unsaturated dianhydride, a bis-unsaturated derivative, a bis-halohydrin, a bis-azetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyamino amide; these polyamino amides can be alkylated or, if they contain one or more tertiary amine functions, they can be quaternized. Such polymers are described, in particular, in French patents 2 252 840 and 2 368 508.

(7) Cyclopolymers of alkyldiallylamine or of dialkyldiallylammonium, such as the homopolymers or copolymers containing, as a main constituent of the chain, units corresponding to formula (V) or (VI):

(V)

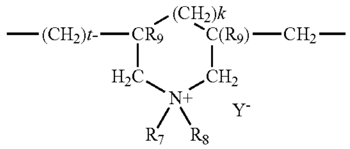

(VI)

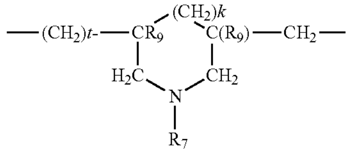

in which formulae k and t are equal to 0 or 1, the sum k+t being equal to 1; $R_9$ denotes a hydrogen atom or a methyl radical; $R_7$ and $R_8$, independently of each other, denote an alkyl group having from 1 to 6 carbon atoms, a hydroxyalkyl group in which the alkyl group preferably has 1 to 5 carbon atoms, a lower ($C_1$-$C_4$) amidoalkyl group, or $R_7$ and $R_8$ can denote, together with the nitrogen atom to which they are attached, heterocyclic groups such as piperidyl or morpholinyl; $R_7$ and $R_8$, independently of each other, preferably denote an alkyl group having from 1 to 4 carbon atoms; and $Y^-$ is an anion such as bromide, chloride, acetate, borate, citrate, tartrate, bisulfate, bisulfite, sulfate or phosphate. These polymers are described in particular in French patent 2 080 759 and in its Certificate of Addition 2 190 406.

Among the polymers defined above, mention may more particularly be made of the dimethyldiallylammonium chloride homopolymer sold under the name "Merquat 100" by the company Nalco (and its homologues of low weight-average molecular mass) and the copolymers of diallyldimethylammonium chloride and of acrylamide, sold under the name "Merquat 550".

(8) The quaternary diammonium polymer containing repeating units corresponding to the formula:

(VII)

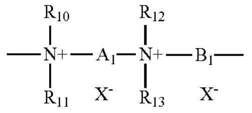

in which formula (VII):

$R_{10}$, $R_{11}$, $R_{12}$ and Rn, which may be identical or different, represent aliphatic, alicyclic or arylaliphatic radicals containing from 1 to 20 carbon atoms or lower hydroxyalkylaliphatic radicals, or alternatively $R_{10}$, $R_{11}$, $R_{12}$ and Rn, together or separately, constitute, with the nitrogen atoms to which they are attached, heterocycles optionally containing a second hetero atom other than nitrogen, or alternatively $R_{10}$, $R_{11}$, $R_{12}$ and $R_{13}$ represent a linear or branched $C_1$-$C_6$ alkyl radical substituted with a nitrile, ester, acyl or amide group or a group —CO—O—$R_{14}$-D or —CO—NH—$R_{14}$-D where $R_{14}$ is an alkylene and D is a quaternary ammonium group;

$A_1$ and $B_1$ represent polymethylene groups containing from 2 to 20 carbon atoms which may be linear or branched, saturated or unsaturated, and which may contain, linked to or intercalated in the main chain, one or more aromatic rings or one or more oxygen or sulfur atoms or sulfoxide, sulfone, disulfide, amino, alkylamino, hydroxyl, quaternary ammonium, ureido, amide or ester groups, and $X^-$ denotes an anion derived from an inorganic or organic acid;

$A_1$, $R_{10}$ and $R_{12}$ can form, with the two nitrogen atoms to which they are attached, a piperazine ring; in addition, if $A_1$ denotes a linear or branched, saturated or unsaturated alkylene or hydroxyalkylene radical, $B_1$ can also denote the group $—(CH_2)_n—CO\text{-}D\text{-}OC—(CH_2)_n—$ in which D denotes:

i) a glycol residue of formula: —O—Z—O—, where Z denotes a linear or branched hydrocarbon-based radical or a group corresponding to one of the following formulae:

$$—(CH_2—CH_2—O)_x—CH_2—CH_2—; \text{ and}$$

$$—[CH_2—CH(CH_3)—O]_y—CH_2—CH(CH_3)—$$

where x and y denote an integer from 1 to 4, representing a defined and unique degree of polymerization or any number from 1 to 4 representing an average degree of polymerization;

ii) a bis-secondary diamine residue such as a piperazine derivative;

iii) a bis-primary diamine residue of formula —NH—Y—NH—, where Y denotes a linear or branched hydrocarbon-based radical, or alternatively the divalent radical $—CH_2—CH_2—S—S—CH_2—CH_2—$; or iv) a ureylene group of formula —NH—CO—NH—.

Preferably, $X^-$ is an anion such as chloride or bromide.

These polymers generally have a number-average molecular mass of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945, and 4,027,020.

It is more particularly possible to use polymers that consist of repeating units corresponding to the following formula (VIII):

(VIII)

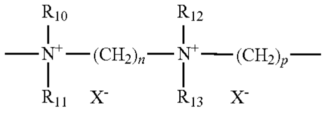

in which $R_{10}$, $R_{11}$, $R_{12}$ and $R_{13}$, which may be identical or different, denote an alkyl or hydroxyalkyl radical containing from 1 to 4 carbon atoms approximately, n and p are integers ranging from 2 to 20 approximately, and $X^-$ is an anion derived from a mineral or organic acid.

One particularly preferred compound of formula (VIII) is that for which $R_{10}$, $R_{11}$, $R_{12}$ and $R_{13}$ represent a methyl group, n=3, p=6 and X═Cl, which is called Hexadimethrine chloride according to the INCI (CTFA) nomenclature.

(9) Polyamines such as Polyquart H sold by Cognis, which is given under the reference name "Polyethylene glycol (15) tallow polyamine" in the CTFA dictionary.

(10) Crosslinked methacryloyloxy($C_1$-$C_4$)alkyltri($C_1$-$C_4$)alkylammonium salt polymers such as the polymers obtained by homopolymerization of dimethylaminoethyl methacrylate quaternized with methyl chloride, or by copolymerization of acrylamide with dimethylaminoethyl methacrylate quaternized with methyl chloride, the homo- or copolymerization being followed by crosslinking with a compound containing olefinic unsaturation, in particular methylenebisacrylamide. A crosslinked acrylamide/methacryloyloxyethyltrimethylammonium chloride copolymer (20/80 by weight) in the form of a dispersion containing 50% by weight of the said copolymer in mineral oil can be used more particularly. This dispersion is sold under the name "Salcare® SC 92" by the company BASF. A crosslinked methacryloyloxyethyltrimethylammonium chloride homopolymer containing about 50% by weight of the homopolymer in mineral oil or in a liquid ester can also be used. These dispersions are sold under the names "Salcare® SC 95" and "Salcare® SC 96" by the company Allied Colloids.

(11) Other cationic polymers which can be used in the context of the present invention are polyalkyleneimines, in particular polyethyleneimines, polymers containing vinylpyridine or vinylpyridinium units, condensates of polyamines and of epichlorohydrin, quaternary polyureylenes and chitin derivatives.

It is preferable that, the cationic polymer be a polyquaternium polymer or a polymeric quaternary ammonium salt.

Polymeric quaternary ammonium salts are cationic polymers comprising at least one quaternized nitrogen atom. Mention may in particular be made, as polymeric quaternary ammonium salts, of the Polyquaternium products (CTFA name), which contribute mainly to the quality of foam and feeling of the skin after use, in particular the feeling of the skin after use. These polymers can preferably be chosen from the following polymers:

Polyquaternium-5, such as the product Merquat 5 sold by Nalco;

Polyquaternium-6, such as the product Salcare SC 30 sold by BASF and the product Merquat 100 sold by Nalco;

Polyquaternium-7, such as the products Merquat S, Merquat 2200, Merquat 7SPR, and Merquat 550 sold by Nalco and the product Salcare SC 10 sold by BASF;

Polyquatemium-10, such as the product Polymer JR400 sold by Amerchol;

Polyquatemium-11, such as the products Gafquat 755, Gafquat 755N and Gafquat 734 sold by ISP;

Polyquaternium-15, such as the product Rohagit KF 720 F sold by Rohm;

Polyquatemium-16, such as the products Luviquat FC905, Luviquat FC370, Luviquat HM552 and Luviquat FC550 sold by BASF;

Polyquaternium-28, such as the product Styleze CC10 sold by ISP;

Polyquaternium-44, such as the product Luviquat Care sold by BASF;

Polyquaternium-46, such as the product Luviquat Hold sold by BASF; and

Polyquaternium-47, such as the product Merquat 2001 sold by Nalco.

The amount of the cationic polymer(s) in the composition according to the present invention may be 0.01% by weight or more, preferably 0.05% by weight or more, and more preferably by weight or more, relative to the total weight of the composition. It is even more preferable that the amount of the cationic polymer(s) in the composition according to the present invention be 0.5% by weight or more, relative to the total weight of the composition.

On the other hand, the amount of the cationic polymer(s) in the composition according to the present invention may be 15% by weight or less, preferably 10% by weight or less, and more preferably 5% by weight or less, relative to the total weight of the composition. It is even more preferable that the amount of the cationic polymer(s) in the composition according to the present invention be 2% by weight or less, relative to the total weight of the composition.

The amount of the cationic polymer(s) in the composition according to the present invention may be from 0.01% to 15% by weight, preferably from 0.05% to 10% by weight, and more preferably from 0.1% to 5% by weight, relative to the total weight of the composition. It is even more preferable that the amount of the cationic polymer(s) in the composition according to the present invention be from 0.5% to 2% by weight, relative to the total weight of the composition.

(Nonionic Surfactant)

The composition according to the present invention may comprise at least one nonionic surfactant. A single type of nonionic surfactant may be used, but two or more different types of nonionic surfactants may be used in combination.

The nonionic surfactant may have an HLB (Hydrophilic Lipophilic Balance) value of from 3.0 to 7.0, preferably from 3.5 to 6.0, and more preferably from 4.0 to 5.0. Alternatively, the nonionic surfactant may have an HLB value of from 11 to 1.7, preferably from 12 to 16, and more preferably from 13 to 15. If two or more nonionic surfactants are used, the HLB value is determined by the weighted average of the HLB values of all the nonionic surfactants.

The nonionic surfactant may be chosen from:

(1) surfactants chosen from polyglyceryl fatty acid esters, polyoxyalkylenated alkyl 50 glycerides, and polyoxyalkylenated fatty ethers;

(2) mixed esters of fatty acid or of fatty alcohol, of carboxylic acid and of glycerol;

(3) fatty acid esters of sugars and fatty alcohol ethers of sugars;

(4) surfactants chosen from fatty esters of sorbitan and oxyalkylenated fatty esters of sorbitan, and oxyalkylenated fatty esters;

(5) block copolymers of ethylene oxide (A) and of propylene oxide (B), (6) polyoxyethylenated (1-40 EO) and polyoxypropylenated (1-30 PO) alkyl ($C_{16}$-$C_{30}$) ethers, (7) silicone surfactants, and (8) mixtures thereof.

The surfactant (1) may be a fluid at a temperature of less than or equal to 45° C.

The surfactant (1) may be in particular:

polyglyceryl fatty acid esters of at least one, preferably one, fatty acid comprising at least one saturated or unsaturated, linear or branched $C_8$-$C_{22}$ hydrocarbon group such as $C_8$-$C_{22}$ alkyl or alkenyl group, preferably $C_8$-$C_{18}$ alkyl or alkenyl group, and more preferably $C_8$-$C_{12}$ alkyl or alkenyl group, and of 2-12 glycerols, preferably 2-10 glycerols and more preferably 2-8 glycerols;

polyoxyethylenated (PEGylated) alkyl glycerides such as polyethylene glycol derivatives of a mixture of mono-, di- and tri-glycerides of caprylic and capric acids (preferably 2 to 30 ethylene oxide units, more preferably 2 to 20 ethylene oxide units, and even more preferably 2 to 10 ethylene oxide units), e.g., PEG-6 Caprylic/Capric Glycerides, PEG-7 Caprylic/Capric Glycerides, and PEG-7 glyceryl cocoate;

polyoxyethylenated fatty ethers of at least one, preferably one, fatty alcohol comprising at least one saturated or unsaturated, linear or branched $C_8$-$C_{22}$ hydrocarbon group such as $C_8$-$C_{22}$ alkyl or alkenyl group, preferably $C_8$-$C_{18}$ alkyl or alkenyl group, and more preferably $C_8$-$C_{12}$ alkyl or alkenyl group, and of 2 to 60 ethylene oxides, preferably from 2 to 30 ethylene oxides, and more preferably from 2 to 10 ethylene oxides; and mixtures thereof.

It is preferable that the polyglyceryl fatty acid ester have a polyglycerol moiety derived from 2 to 10 glycerols, more preferably from 2 to 8 glycerols, and further more preferably 4 to 6 glycerols.

The polyglyceryl fatty acid ester may be chosen from the mono, di and tri esters of saturated or unsaturated acid, preferably saturated acid, including 8 to 22 carbon atoms, preferably 8 to 18 carbon atoms, and more preferably 8 to 12 carbon atoms, such as caprylic acid, capric acid, lauric acid, oleic acid, stearic acid, isostearic acid, and myristic acid.

The polyglyceryl fatty acid ester may be selected from the group consisting of PG2 caprate, PG2 dicaprate, PG2 tricaprate, PG2 caprylate, PG2 dicaprylate, PG2 tricaprylate, PG2 laurate, PG2 dilaurate, PG2 trilaurate, PG2 myristate, PG2 dimyristate, PG2 trimyristate, PG2 stearate, PG2 distearate, PG2 tristearate, PG2 isostearate, PG2 diisostearate, PG2 triisostearate, PG2 oleate, PG2 dioleate, PG2 trioleate, PG3 caprate, PG3 dicaprate, PG3 tricaprate, PG3 caprylate, PG3 dicaprylate, PG3 tricaprylate, PG3 laurate, PG3 dilaurate, PG3 trilaurate, PG3 myristate, PG3 dimyristate, PG3 trimyristate, PG3 stearate, PG3 distearate, PG3 tristearate, PG3 isostearate, PG3 diisostearate, PG3 triisostearate, PG3 oleate, PG3 dioleate, PG3 trioleate, PG4 caprate, PG4 dicaprate, PG4 tricaprate, PG4 caprylate, PG4 dicaprylate, PG4 tricaprylate, PG4 laurate, PG4 dilaurate, PG4 trilaurate, PG4 myristate, PG4 dimyristate, PG4 trimyristate, PG4 stearate, PG4 distearate, PG4 tristearate, PG4 isostearate, PG4 diisostearate, PG4 triisostearate, PG4 oleate, PG4 dioleate, PG4 trioleate, PG5 caprate, PG5 dicaprate, PG5 tricaprate, PG5 caprylate, PG5 dicaprylate, PG5 tricaprylate, PG5 laurate, PG5 dilaurate, PG5 trilaurate, PG5 myristate, PG5 dimyristate, PG5 trimyristate, PG5 stearate, PG5 distearate, PG5 tristearate, PG5 isostearate, PG5 diisostearate, PG5 triisostearate, PG5 oleate, PG5 dioleate, PG5 trioleate, PG6 caprate, PG6 dicaprate, PG6 tricaprate, PG6 caprylate, PG6 dicaprylate, PG6 tricaprylate, PG6 laurate, PG6 dilaurate, PG6 trilaurate, PG6 myristate, PG6 dimyristate, PG6 trimyristate, PG6 stearate, PG6 distearate, PG6 tristearate, PG6 isostearate, PG6 diisostearate, PG6 triisostearate, PG6 oleate, PG6 dioleate, PG6 trioleate, PG10 caprate, PG10 dicaprate, PG10 tricaprate, PG10 caprylate, PG10 dicaprylate, PG10 tricaprylate, PG10 laurate, PG10 dilaurate, PG10 trilaurate, PG10 myristate, PG10 dimyristate, PG10 trimyristate, PG10 stearate, PG10 distearate, PG10 tristearate, PG10 isostearate, PG10 diisostearate, PG10 triisostearate, PG10 oleate, PG10 dioleate, and PG10 trioleate.

The polyoxyalkylenated fatty ethers, preferably polyoxyethylenated fatty ethers, may comprise from 2 to 60 ethylene oxide units, preferably from 2 to 30 ethylene oxide units, and more preferably from 2 to 10 ethylene oxide units. The fatty chain of the ethers may be chosen in particular from lauryl, behenyl, arachidyl, stearyl and cetyl units, and mixtures thereof, such as cetearyl. Examples of ethoxylated fatty ethers which may be mentioned are lauryl alcohol ethers comprising 2, 3, 4, and 5 ethylene oxide units (CTFA names: Laureth-2, Laureth-3, Laureth-4, and Laureth-5), such as the products sold under the names Nikkol BL-2 by the company Nikko Chemicals, Emalex 703 by the company Nihon Emulsion Co., Ltd, Nikkol BL-4 by the company Nikko Chemicals, and EMALEX 705 by the company Nihon Emulsion Co., Ltd. Mention may also be made of, for example, stearyl alcohol ethers comprising 2, 3, 4 and 5 ethylene oxide units (CTFA names: Steareth-2, Steareth-3, Steareth-4, and Steareth-5), such as the products sold under the names Emalex 602 by the company Nihon Emulsion Co., Ltd., Emalex 603 by the company Nihon Emulsion Co., Ltd, Nikkol BS-4 by the company Nikko Chemicals, and Emalex 605 by the company Nihon Emulsion Co., Ltd.

The (2) mixed esters of fatty acids, or of fatty alcohol, of carboxylic acid and of glycerol, which can be used as the above nonionic surfactant, may be chosen in particular from the group comprising mixed esters of fatty acid or of fatty alcohol with an alkyl or alkenyl chain containing from 8 to 22 carbon atoms, preferably from 8 to 18 carbon atoms, and more preferably from 8 to 12 carbon atoms, and of α-hydroxy acid and/or of succinic acid, with glycerol. The α-hydroxy acid may be, for example, citric acid, lactic acid, glycolic acid or malic acid, and mixtures thereof.

The alkyl chain of the fatty acids or alcohols from which are derived the mixed esters which can be used in the nanoemulsion of the present invention may be linear or branched, and saturated or unsaturated. They may especially be stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures thereof.

As examples of mixed esters which can be used in the nanoemulsion of the present invention, mention may be made of the mixed ester of glycerol and of the mixture of citric acid, lactic acid, linoleic acid and oleic acid (CTFA name: Glyceryl citrate/lactate/linoleate/oleate) sold by the company Hüls under the name Imwitor 375; the mixed ester of succinic acid and of isostearyl alcohol with glycerol (CTFA name: Isostearyl diglyceryl succinate) sold by the company Hüls under the name Imwitor 780 K; the mixed ester of citric acid and of stearic acid with glycerol (CTFA name: Glyceryl stearate citrate) sold by the company Hills under the name Imwitor 370; the mixed ester of lactic acid and of stearic acid with glycerol (CTFA name: Glyceryl stearate lactate) sold by the company Danisco under the name Lactodan B30 or Rylo LA30.

The (3) fatty acid esters of sugars, which can be used as the above nonionic surfactant, may be chosen in particular from the group comprising esters or mixtures of esters of $C_8$-$C_{22}$ fatty acid and of sucrose, of maltose, of glucose or of fructose, and esters or mixtures of esters of $C_{14}$-$C_{22}$ fatty acid and of methylglucose.

The $C_8$-$C_{22}$ or $C_{14}$-$C_{22}$ fatty acids forming the fatty unit of the esters which can be used in the present invention comprise a saturated or unsaturated linear alkyl or alkenyl chain containing, respectively, from 8 to 22 or from 14 to 22 carbon atoms. The fatty unit of the esters may be chosen in particular from stearates, behenates, arachidonates, palmitates, myristates, laurates and caprates, and mixtures thereof. Stearates are preferably used.

As examples of esters or mixtures of esters of fatty acid and of sucrose, of maltose, of glucose or of fructose, mention may be made of sucrose monostearate, sucrose distearate and sucrose tristearate and mixtures thereof, such as the products sold by the company Croda under the name Crodesta F50, F70, F110 and F160; and examples of esters or mixtures of esters of fatty acid and of methylglucose which may be mentioned are methylglucose polyglyceryl-3 distearate, sold by the company Goldschmidt under the name Tego-care 450. Mention may also be made of glucose or maltose monoesters such as methyl o-hexadecanoyl-6-D-glucoside and o-hexadecanoyl-6-D-maltoside.

The (3) fatty alcohol ethers of sugars, which can be used as the above nonionic surfactant, may be solid at a temperature of less than or equal to 45° C. and may be chosen in particular from the group comprising ethers or mixtures of ethers of $C_8$-$C_{22}$ fatty alcohol and of glucose, of maltose, of sucrose or of fructose, and ethers or mixtures of ethers of a $C_{14}$-$C_{22}$ fatty alcohol and of methylglucose. These are in particular alkylpolyglucosides.

The $C_8$-$C_{22}$ or $C_{14}$-$C_{22}$ fatty alcohols forming the fatty unit of the ethers which may be used in the nanoemulsion of the present invention comprise a saturated or unsaturated, linear alkyl or alkenyl chain containing, respectively, from 8 to 22 or from 14 to 22 carbon atoms. The fatty unit of the ethers may be chosen in particular from decyl, cetyl, behenyl, arachidyl, stearyl, palmityl, myristyl, lauryl, capryl and hexadecanoyl units, and mixtures thereof, such as cetearyl.

As examples of fatty alcohol ethers of sugars, mention may be made of alkylpolyglucosides such as decylglucoside and laurylglucoside, which is sold, for example, by the company Henkel under the respective names Plantaren 2000 and Plantaren 1200, cetostearyl glucoside optionally as a mixture with cetostearyl alcohol, sold for example, under the name Montanov 68 by the company SEPPIC, under the name Tego-care CG90 by the company Goldschmidt and under the name Emulgade KE3302 by the company Henkel, as well as arachidyl glucoside, for example in the form of a mixture of arachidyl alcohol and behenyl alcohol and arachidyl glucoside, sold under the name Montanov 202 by the company SEPPIC.

The surfactant used more particularly is sucrose monostearate, sucrose distearate or sucrose tristearate and mixtures thereof, methylglucose polyglyceryl-3 distearate and alkylpolyglucosides.

The (4) fatty esters of sorbitan and oxyalkylenated fatty esters of sorbitan which may be used as the above nonionic surfactant may be chosen from the group comprising $C_{16}$-$C_{22}$ fatty acid esters of sorbitan and oxyethylenated $C_{16}$-$C_{22}$ fatty acid esters of sorbitan. They may be formed from at least one fatty acid comprising at least one saturated linear alkyl chain containing, respectively, from 16 to 22 carbon atoms, and from sorbitol or from ethoxylated sorbitol. The oxyethylenated esters may generally comprise from 1 to 100 ethylene glycol units and preferably from 2 to 40 ethylene oxide (EO) units.

These esters may be chosen in particular from stearates, behenates, arachidates, palmitates, and mixtures thereof. Stearates and palmitates are preferably used.

As examples of the above nonionic surfactant which can be used in the present invention, mention may be made of sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65.

The (4) oxyalkylenated fatty esters, preferably ethoxylated fatty esters, which may be used as the above nonionic surfactant, may be esters formed from 1 to 100 ethylene oxide units, preferably from 2 to 60 ethylene oxide units, and more preferably from 2 to 30 ethylene oxide units, and from at least one fatty acid chain containing from 8 to 22 carbon atoms, preferably from 8 to 18 carbon atoms, and more preferably from 8 to 12 carbon atoms. The fatty chain in the esters may be chosen in particular from stearate, behenate, arachidate and palmitate units, and mixtures thereof. Examples of ethoxylated fatty esters which may be mentioned are the ester of stearic acid comprising 40 ethylene oxide units, such as the product sold under the name Myrj 52 (CTFA name: PEG-40 stearate) by the company ICI, as well as the ester of behenic acid comprising 8 ethylene oxide units (CTFA name: PEG-8 behenate), such as the product sold under the name Compritol HD5 ATO by the company Gattefosse.

The (5) block copolymers of ethylene oxide (A) and of propylene oxide (B), which may be used as the above nonionic surfactant, may be chosen in particular from block copolymers of formula (I):

$$HO(C_2H_4O)_x(C_3H_6O)_y(C_2H_4O)_zH \qquad (I)$$

in which x, y and z are integers such that x+z ranges from 2 to 100 and y ranges from 14 to 60, and mixtures thereof, and more particularly from the block copolymers of formula (I) having an HLB value ranging from 8.0 to 14.0.

The (6) polyoxyethylenated (1-40 EO) and polyoxypropylenated (1-30 PO) alkyl ($C_{16}$-$C_{30}$) ethers, which may be used as the above nonionic surfactant, may be selected from the group consisting of:

- PPG-6 Decyltetradeceth-30; Polyoxyethylene (30) Polyoxypropylene (6) Tetradecyl Ether such as those sold as Nikkol PEN-4630 from Nikko Chemicals Co.,
- PPG-6 Decyltetradeceth-12; Polyoxyethylene (12) Polyoxypropylene (6) Tetradecyl Ether 50 such as those sold as Nikkol PEN-4612 from Nikko Chemicals Co.,
- PPG-13 Decyltetradeceth-24; Polyoxyethylene (24) Polyoxypropylene (13) Decyltetradecyl Ether such as those sold as UNILUBE 50MT-2200B from NOF Corporation,
- PPG-6 Decyltetradeceth-20; Polyoxyethylene (20) Polyoxypropylene (6) Decyltetradecyl Ether such as those sold as Nikkol PEN-4620 from Nikko Chemicals Co.,
- PPG-4 Ceteth-1; Polyoxyethylene (1) Polyoxypropylene (4) Cetyl Ether such as those sold as Nikkol PBC-31 from Nikko Chemicals Co.,
- PPG-8 Ceteth-1; Polyoxyethylene (1) Polyoxypropylene (8) Cetyl Ether such as those sold as Nikkol PBC-41 from Nikko Chemicals Co.,
- PPG-4 Ceteth-10; Polyoxyethylene (10) Polyoxypropylene (4) Cetyl Ether such as those sold as Nikkol PBC-33 from Nikko Chemicals Co.,
- PPG-4 Ceteth-20; Polyoxyethylene (20) Polyoxypropylene (4) Cetyl Ether such as those sold as Nikkol PBC-34 from Nikko. Chemicals Co.,
- PPG-5 Ceteth-20; Polyoxyethylene (20) Polyoxypropylene (5) Cetyl Ether such as those sold as Procetyl AWS from Croda Inc.,
- PPG-8 Ceteth-20; Polyoxyethylene (20) Polyoxypropylene (8) Cetyl Ether such as those sold as Nikkol PBC-44 from Nikko Chemicals Co., and
- PPG-23 Steareth-34; Polyoxyethylene Polyoxypropylene Stearyl Ether (34 EO) (23 PO) such as those sold as Unisafe 34S-23 from Pola Chemical Industries. They can provide a composition with stability over a long time, even though the temperature of the composition is increased and decreased in a relatively short period of time.

It is more preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-6 Decyltetradeceth-20, PPG-5 Ceteth-20, PPG-8 Ceteth-20 and PPG-23 Steareth-34.

It is even more preferable that the polyoxyethylenated (1-40 EO) and polyoxypropylenated (1-30 PO) alkyl ($C_{16}$-$C_{30}$) ethers are (15-40 EO) and polyoxypropylenated (5-30 PO) alkyl ($C_{16}$-$C_{24}$) ethers, which could be selected from the group consisting of PPG-6 Decyltetradeceth-30, PPG-13 Decyltetradeceth-24, PPG-5 Ceteth-20, and PPG-8 Ceteth-20.

As (7) silicone surfactants, which may be used as the above nonionic surfactant, mention may be made of those disclosed in documents U.S. Pat. Nos. 5,364,633 and 5,411,744.

The (7) silicone surfactant as the above nonionic surfactant may preferably be a compound of formula (I):

(I)

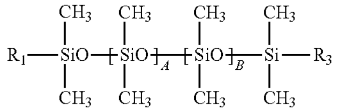

in which:

- $R_1$, $R_2$ and $R_3$, independently of each other, represent a $C_1$-$C_6$ alkyl radical or a radical $-(CH_2)_x-(OCH_2CH_2)_y-(OCH_2CH_2CH_2)_z-OR_4$, at least one radical $R_1$, $R_2$ or $R_3$ not being an alkyl radical; $R_4$ being a hydrogen, an alkyl radical or an acyl radical;
- A is an integer ranging from 0 to 200;
- B is an integer ranging from 0 to 50; with the proviso that A and B are not simultaneously equal to zero;
- x is an integer ranging from 1 to 6;
- y is an integer ranging from 1 to 30;
- z is an integer ranging from 0 to 5.

According to one preferred embodiment of the present invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

(II)

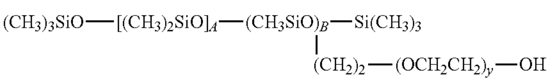

in which A is an integer ranging from 20 to 105, B is an integer ranging from 2 to 10 and y is an integer ranging from 10 to 20.

As examples of silicone surfactants of formula (I), mention may also be made of the compounds of formula (III):

$$H-(OCH_2CH_2)_y-(CH_2)_3-[(CH_3)_2SiO]_{A'}-(CH_2)_3-(OCH_2CH_2)_y-OH$$

in which A' and y are integers ranging from 10 to 20.

Compounds of the present invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

The amount of the nonionic surfactant(s) in the composition according to the present invention may be 0.1% by weight or more, preferably 0.5% by weight or more, and more preferably 1% by weight or more relative to the total weight of the composition.

On the other hand, the amount of the nonionic surfactant(s) in the composition according to the present invention may be 15% by weight or less, preferably 10% by weight or less, and more preferably 5% by weight or less relative to the total weight of the composition.

The amount of the nonionic surfactant(s) in the composition according to the present invention may range from 0.1% to 15% by weight, preferably from 0.5% to 10% by weight, more preferably from 1% to 5% by weight relative to the total weight of the composition.

(Thickening Agent)

The composition according to the present invention may comprise at least one thickening agent. A single type of thickening agent may be used, but two or more different types of thickening agent may be used in combination.

It is preferable that the thickening agent be selected from the group consisting of:

(i) associative thickeners;

(ii) crosslinked acrylic acid homopolymers;

(iii) crosslinked copolymers of (meth)acrylic acid and of ($C_1$-$C_6$)alkyl acrylate;

(iv) nonionic homopolymers and copolymers comprising ethylenically unsaturated monomers of ester and/or amide type;

(v) ammonium acrylate homopolymers and copolymers of ammonium acrylate and of acrylamide;

(vi) polysaccharides; and (vii) $C_{12}$-$C_{30}$ fatty alcohols.

(i) As used herein, the expression "associative thickener" means an amphiphilic thickener comprising both hydrophilic units and hydrophobic units, for example, at least one $C_8$-$C_{30}$ fatty chain and at least one hydrophilic unit.

Representative associative thickeners that may be used are associative polymers chosen from:

(aa) nonionic amphiphilic polymers comprising at least one fatty chain and at least one hydrophilic unit;

(bb) anionic amphiphilic polymers comprising at least one hydrophilic unit and at least one fatty-chain unit;

(cc) cationic amphiphilic polymers comprising at least one hydrophilic unit and at least one fatty-chain unit; and (dd) amphoteric amphiphilic polymers comprising at least one hydrophilic unit and at least one fatty-chain unit, wherein the fatty chain contains from 10 to 30 carbon atoms.

The (aa) nonionic amphiphilic polymers comprising at least one fatty chain and at least one hydrophilic unit may, for example, be chosen from:

(1) celluloses modified with groups comprising at least one fatty chain; examples that may be mentioned include:

hydroxyethylcelluloses modified with groups comprising at least one fatty chain chosen from alkyl, arylalkyl, and alkylaryl groups, and in which the alkyl groups are, for example, $C_8$-$C_{22}$, such as the product Natrosol Plus Grade 330 CS($C_1$-$C_6$ alkyls) sold by the company Aqualon, and the product Bermocoll EHM 100 sold by the company Berol Nobel, and celluloses modified with polyalkylene glycol alkylphenyl ether groups, such as the product Amercell Polymer HM-1500 (polyethylene glycol (15) nonylphenyl ether) sold by the company Amerchol.

(2) hydroxypropyl guars modified with groups comprising at least one fatty chain, such as the product Esaflor HM 22 ($C_{22}$ alkyl chain) sold by the company Lamberti, and the products Miracare XC95-3 ($C_{14}$ alkyl chain) and RE205-1 ($C_{20}$ alkyl chain) sold by the company Rhodia Chimie.

(3) polyether urethanes comprising at least one fatty chain, such as $C_{10}$-$C_{30}$ alkyl or alkenyl groups, for instance the products Elfacos T 210 and Elfacos T 212 sold by the company Akzo or the products Aculyn 44 and Aculyn 46 sold by the company Rohm & Haas.

(4) copolymers of vinylpyrrolidone and of hydrophobic fatty-chain monomers; examples that may be mentioned include:

the products Antaron V216 and Ganex V216 (vinylpyrrolidone/hexadecene copolymer) sold by the company I.S.P., and the products Antaron V220 and Ganex V220 (vinylpyrrolidone/eicosene copolymer) sold by the company I.S.P.

(5) copolymers of $C_1$-$C_6$ alkyl acrylates or methacrylates and of amphiphilic monomers comprising at least one fatty chain, such as the oxyethylenated methyl methacrylate/stearyl acrylate copolymer sold by the company Goldschmidt under the name Antil 208.

(6) copolymers of hydrophilic acrylates or methacrylates and of hydrophobic monomers comprising at least one fatty chain, such as a polyethylene glycol methacrylate/lauryl methacrylate copolymer.

The (bb) anionic amphiphilic polymers comprising at least one hydrophilic unit and at least one fatty-chain unit, may, for example, be chosen from those comprising at least one fatty-chain allyl ether unit and at least one hydrophilic unit comprising an ethylenic unsaturated anionic monomeric unit, for example, a vinylcarboxylic acid unit and further, for example, be chosen from units derived from acrylic acids, methacrylic acids, and mixtures thereof, wherein the fatty-chain allyl ether unit corresponds to the monomer of formula (I) below:

$$CH_2{=}C(R_1)CH_2OB_nR \quad (I)$$

in which $R_1$ is chosen from H and $CH_3$, B is an ethyleneoxy radical, n is chosen from zero and integers ranging from 1 to 100, R is chosen from hydrocarbon-based radicals chosen from alkyl, arylalkyl, aryl, alkylaryl, and cycloalkyl radicals, containing from 10 to 30 carbon atoms, and further, for example, from 10 to 24 carbon atoms and even further, for example, from 12 to 18 carbon atoms.

In one embodiment, a unit of formula (I) is, for example, a unit in which $R_1$ can be H, n can be equal to 10, and R can be a stearyl ($C_{18}$) radical.

Anionic amphiphilic polymers of this type are described and prepared, according to an emulsion polymerization process, in patent EP-0 216 479 B2.

In one embodiment, anionic amphiphilic polymers are, for example, polymers formed from 20% to 60% by weight of acrylic acid and/or of methacrylic acid, from 5% to 60% by weight of lower alkyl (meth)acrylates, from 2% to 50% by weight of fatty-chain allyl ether of formula (I), and from 0% to 1% by weight of a crosslinking agent which is a well-known copolymerizable unsaturated polyethylenic monomer, for example, diallyl phthalate, allyl(meth)acrylate, divinylbenzene, (poly)ethylene glycol dimethacrylate, and methylenebisacrylamide.

Examples of such polymers are crosslinked terpolymers of methacrylic acid, of ethyl acrylate, and of polyethylene glycol (10 EO) stearyl ether (Steareth-10), such as those sold by the company Ciba under the names Salcare SC 80 and Salcare SC 90, which are aqueous 30% emulsions of a crosslinked terpolymer of methacrylic acid, of ethyl acrylate, and of steareth-allyl ether (40/50/10).

The anionic amphiphilic polymers may further be chosen, for example, from those comprising at least one hydrophilic unit of unsaturated olefinic carboxylic acid type, and at least one hydrophobic unit of a type such as a ($C_{10}$-$C_{30}$) alkyl ester of an unsaturated carboxylic acid. The hydrophilic unit of unsaturated olefinic carboxylic acid type corresponds to, for example, the monomer of formula (II) below:

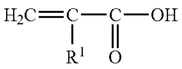

(II)

in which $R^1$ is chosen from H, $CH_3$, and $C_2H_5$, i.e., acrylic acid, methacrylic acid, and methacrylic acid units. The hydrophobic unit of a type such as a ($C_{10}$-$C_{30}$) alkyl ester of an unsaturated carboxylic acid corresponds to, for example, the monomer of formula (III) below:

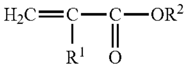

(III)

in which $R^1$ is chosen from H, $CH_3$, and $C_2H_5$ (i.e., acrylate, methacrylate, and methacrylate units) and is, for example, chosen from, for example, H (acrylate units) and $CH_3$ (methacrylate units), and $R^2$ is chosen from $C_{10}$-$C_{30}$ alkyl radicals, for example, $C_{12}$-$C_{22}$ alkyl radicals.

Examples of ($C_{10}$-$C_{30}$)alkyl esters of unsaturated carboxylic acids include lauryl acrylate, stearyl acrylate, decyl acrylate, isodecyl acrylate, and dodecyl acrylate, and the corresponding methacrylates, lauryl methacrylate, stearyl methacrylate, decyl methacrylate, isodecyl methacrylate, and dodecyl methacrylate.

Anionic amphiphilic polymers of this type are disclosed and prepared, for example, according to U.S. Pat. Nos. 3,915,921 and 4,509,949.

Representative anionic amphiphilic polymers that can be used may further be chosen from polymers formed from a mixture of monomers comprising:

(7) acrylic acid, an ester of formula (IV) below:

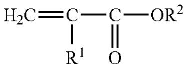

(IV)

in which $R^1$ is chosen from H and $CH_3$, $R^2$ is chosen from $C_{10}$-$C_{30}$ alkyl radicals, such as alkyl radicals containing from 12 to 22 carbon atoms, and a crosslinking agent; such as polymers derived from 95% to 60% by weight of the acrylic acid (hydrophilic unit), 4% to 40% by weight of $C_{10}$-$C_{30}$ alkyl acrylate (hydrophobic unit), and 0% to 6% by weight of crosslinking polymerizable monomer, or polymers derived from 98% to 96% by weight of the acrylic acid (hydrophilic unit), 1% to 4% by weight of $C_{10}$-$C_{30}$ alkyl acrylate (hydrophobic unit), and 0.1% to 0.6% by weight of crosslinking polymerizable monomer; or (8) acrylic acid and lauryl methacrylate, such as the polymers formed from 66% by weight of acrylic acid and 34% by weight of lauryl methacrylate.

The crosslinking agent can be a monomer comprising the group

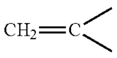

with at least one other polymerizable group whose unsaturated bonds are not conjugated.

Mention may be made, for example, of polyallyl ethers such as polyallylsucrose and polyallylpentaerythritol.

Among said polymers above, mention may be made, for example, of the products sold by the company Goodrich under the trade names Pemulen TR1, Pemulen TR2, and Carbopol 1382, and further, for example, Pemulen TR1, and the product sold by the company S.E.P.C. under the name Coatex SX.

Among anionic amphiphilic fatty-chain polymers, mention may also be made, for example, of the ethoxylated copolymer of methacrylic acid/methyl acrylate/alkyl dimethyl-meta-isopropenylbenzylisocyanate sold under the name Viscophobe DB 1000 by the company Amerchol.

The (cc) cationic amphiphilic polymers used are, for example, chosen from quaternized cellulose derivatives and polyacrylates comprising amino side groups.

The quaternized cellulose derivatives are, for example, chosen from quaternized celluloses modified with groups comprising at least one fatty chain, such as alkyl, arylalkyl, and alkylaryl groups comprising at least 8 carbon atoms, and mixtures thereof, and quaternized hydroxyethylcelluloses modified with groups comprising at least one fatty chain, such as alkyl, arylalkyl, and alkylaryl groups comprising at least 8 carbon atoms, and mixtures thereof.

Quaternized and non-quaternized polyacrylates comprising amino side groups have, for example, hydrophobic groups, such as Steareth 20 (polyoxy-ethylenated(20) stearyl alcohol) and ($C_{10}$-$C_{30}$)alkyl PEG-20 itaconate.

The alkyl radicals borne by the above quaternized celluloses and hydroxyethylcelluloses, for example, contain from 8 to 30 carbon atoms.

The aryl radicals, for example, are chosen from phenyl, benzyl, naphthyl, and anthryl groups.

Examples of quaternized alkylhydroxyethyl-celluloses comprising $C_8$-$C_{30}$ fatty chains are the products Quatrisoft LM 200, Quatrisoft LM-X 529-18-A, Quatrisoft LM-X 529-18B (Cu alkyl), and Quatrisoft LM-X 529-8 ($C_{18}$ alkyl) sold by the company Amerchol, and the products Crodacel QM, Crodacel QL ($C_{12}$ alkyl), and Crodacel QS ($C_{18}$ alkyl) sold by the company Croda.

Examples of polyacrylates comprising amino side chains are the polymers 8781-124B or 9492-103 and Structure Plus from the company National Starch.

Among the (dd) amphoteric amphiphilic polymers comprising at least one hydrophilic unit and at least one fatty-chain unit, mention may be made, for example, of copolymers of methacrylamidopropyltrimethylammonium chloride/acrylic acid/$C_{10}$-$C_{30}$ alkyl methacrylate, wherein the alkyl radical is, for example, a stearyl radical.

The associative thickeners in the compositions can have, for example, in solution or in dispersion at a concentration of 1% active material in water, a viscosity, measured using a Rheomat RM 180 rheometer at 25° C., of greater than 0.1 cp and further, for example, of greater than 0.2 cp, at a shear rate of 200 $s^{-1}$.

The associative thickener may be an associative polymeric thickener, preferably an associative polyurethane thickener.

The associative polyurethane thickener may be cationic or nonionic.

Among the associative polyurethane thickeners, there may be mention of the associative polyurethane derivatives such as those obtained by polymerization: about 20% to 70% by weight of a carboxylic acid containing an $\alpha,\beta$-monoethylenic unsaturation, about 20 to 80% by weight of a nonsurfactant monomer containing an $\alpha,\beta$-monoethylenic unsaturation, about 0.5 to 60% by weight of a nonionic mono-urethane which is the product of the reaction of a monohydroxylated surfactant with a monoethylenically unsaturated monoisocyanate.

The like are described in particular in EP 173109 and more particularly in Example 3 thereof. More precisely, this polymer is a methacrylic acid/methyl acrylate/dimethyl metaisopropenyl benzyl isocyanate of ethoxylated behenyl alcohol (40 EO) terpolymer as an aqueous dispersion at 25%. This product is provided under the reference VISCOPHOBE DB1000 by the company AMERCHOL.

Also suitable are the cationic associative polyurethane thickeners the family of which has been described by the applicant in French Patent Application No. 0009609. They can be represented more particularly by the following general formula (A): $R—X—(P)_n-[L-(Y)_m-]_r-L'-(P')_p—X'—R'$ (A) in which: R and R', which are identical or different, represent a hydrophobic group or a hydrogen atom; X and X', which are identical or different, represent a group containing an amine functional group carrying or otherwise a hydrophobic group, or alternatively the group L"; L, L' and L", which are identical or different, represent a group derived from a diisocyanate; P and P', which are identical or different, represent a group containing an amine functional group carrying or otherwise a hydrophobic group; Y represents a hydrophilic group; r is an integer between 1 and 100, preferably between 1 and 50 and in particular between 1 and 25; n, m and p are each independently of the others between 0 and 1000; the molecule containing at least one protonated or quaternized amine functional group and at least one hydrophobic group.

In a very advantageous embodiment, the only hydrophobic groups of these polyurethanes are the groups R and R' at the chain ends.

According to a first preferred embodiment, the associative polyurethane thickener corresponds to formula (A) in which R and R' both represent independently a hydrophobic group, X, X' each represent a group L", n and p are between 1 and 1000, and L, L', L", P, P', Y and m have the meanings indicated in formula (A).

According to another preferred embodiment of the present invention, the associative polyurethane thickener corresponds to formula (A) in which R and R' both represent independently a hydrophobic group, X, X' each represent a group L", n and p are equal to 0, and L, L', L", Y and m have the meanings in formula (A) indicated above.

The fact that n and p are equal to 0 means that these polymers do not contain units derived from a monomer containing an amine functional group, incorporated into the polymer during polycondensation. The protonated amine functional groups of these polyurethanes result from the hydrolysis of isocyanate functional groups, in excess, at the chain end, followed by alkylation of the primary amine functional groups formed by alkylating agents containing a hydrophobic group, that is to say compounds of the RQ or R'Q type, in which R and R' are as defined above and Q denotes a leaving group such as a halide, a sulfate and the like.

In accordance with another preferred embodiment of the present invention, the associative polyurethane thickener corresponds to formula (A) in which R and R' both represent independently a hydrophobic group, X and X' both represent independently a group containing a quaternary amine, n and p are equal to zero, and L, L', Y and m have the meanings indicated in formula (A).

The number-average molecular mass of the cationic associative polyurethane thickeners is usually between 400 and 500000, in particular between 1000 and 400000, and ideally between 1000 and 300000 g/mol.

When X and/or X' denote a group containing a tertiary or quaternary amine, X and/or X' may represent one of the following formulae:

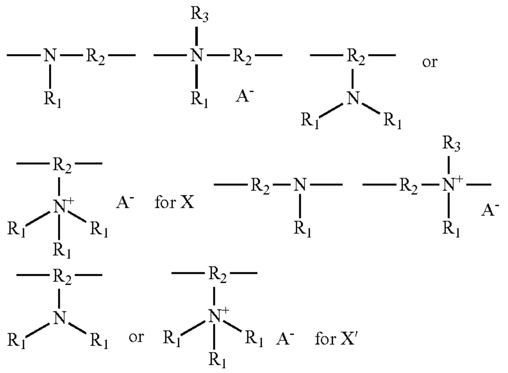

or for X or for X' in which:

$R_2$ represents a linear or branched alkylene radical having from 1 to 20 carbon atoms, containing or otherwise a saturated or unsaturated ring, or an arylene radical, it being possible for one or more of the carbon atoms to be replaced by a heteroatom chosen from N, S, O, P;

$R_1$ and $R_3$, which are identical or different, denote a linear or branched, $C_1$-$C_{30}$ alkyl or alkenyl radical, an aryl radical, it being possible for at least one of the carbon atoms to be replaced by a heteroatom chosen from N, S, O, and P;

$A^-$ is a physiologically acceptable counterion.

The groups L, L' and L" represent a group of formula:

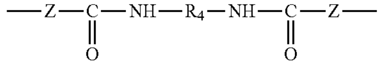

in which:

Z represents —O—, —S— or —NH—; and $R_4$ represents a linear or branched alkylene radical having from 1 to 20 carbon atoms, containing or otherwise a saturated or unsaturated ring, an arylene radical, it being possible for one or more of the carbon atoms to be replaced by a heteroatom chosen from N, S, O and P.

The groups P and P', comprising an amine functional group, may represent at least one of the following formulae:

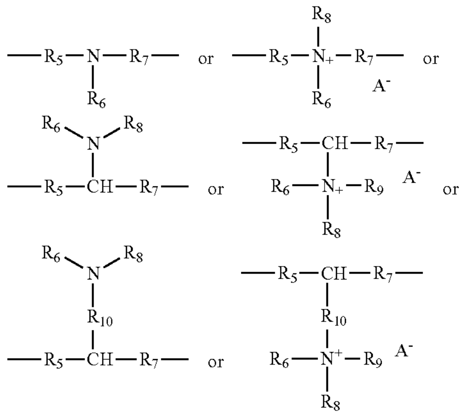

or in which:

$R_5$ and $R_7$ have the same meanings as $R_2$ defined above;

$R_6$, $R_8$ and $R_9$ have the same meanings as $R_1$ and $R_3$ defined above;

$R_{10}$ represents a linear or branched alkylene group, which is optionally unsaturated and which may contain one or more heteroatoms chosen from N, O, S and P;

$A^-$ is a physiologically acceptable counterion.

As regards the meaning of Y, the expression hydrophilic group is understood to mean a polymeric or nonpolymeric water-soluble group. By way of example, there may be mentioned, when polymers are not involved, ethylene glycol, diethylene glycol and propylene glycol. In accordance with a preferred embodiment, in the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The cationic associative polyurethane thickeners of formula (A) are formed from diisocyanates and from various compounds possessing functional groups containing a labile hydrogen. The functional groups containing a labile hydrogen may be alcohol functional groups, primary or secondary amine functional groups or thiol functional groups which give, after reaction with the diisocyanate functional groups, polyurethanes, polyureas and polythioureas, respectively. The term “polyurethanes” of the present invention covers these three types of polymers, namely polyurethanes proper, polyureas and polythioureas and copolymers thereof.

A first type of compounds entering into the preparation of the polyurethane of formula (A) is a compound containing at least one unit containing an amine functional group. This compound may be multifunctional, but preferably the compound is difunctional, that is to say, according to a preferred embodiment, this compound contains two labile hydrogen atoms carried for example by a hydroxyl, primary amine, secondary amine or thiol functional group. It is also possible to use a mixture of multifunctional and difunctional compounds in which the percentage of multifunctional compounds is low.

As indicated above, this compound may contain more than one unit containing an amine functional group. It is then a polymer carrying a repeat of the unit containing an amine functional group.

This type of compound may be represented by one of the following formulae: HZ—$(P)_n$—ZH, or HZ—$(P')_p$—ZH, in which Z, P, P', n and p are as defined above.

By way of example of a compound containing an amine functional group, there may be mentioned N-methyldiethanolamine, N-tert-butyldiethanolamine, and N-sulfoethyldiethanolamine.

The second compound entering into the preparation of the polyurethane of formula (A) is a diisocyanate corresponding to the formula O═C═N—$R_4$—N═C═O in which $R_4$ is defined above.

By way of example, there may be mentioned methylenediphenyl diisocyanate, methylenecyclohexane diisocyanate, isophorone diisocyanate, toluene diisocyanate, naphthalene diisocyanate, butane diisocyanate, and hexane diisocyanate.

A third compound entering into the preparation of the polyurethane of formula (A) is a hydrophobic compound intended to form the terminal hydrophobic groups of the polymer of formula (A).

This compound consists of a hydrophobic group and a functional group containing a labile hydrogen, for example a hydroxyl, primary or secondary amine, or thiol functional group.

By way of example, this compound may be a fatty alcohol, such as, in particular, stearyl alcohol, dodecyl alcohol, and decyl alcohol. When this compound contains a polymeric chain, it may be for example a hydroxyl hydrogenated polybutadiene.

The hydrophobic group of the polyurethane of formula (A) may also result from the quaternization reaction of the tertiary amine of the compound containing at least one tertiary amine unit. Thus, the hydrophobic group is introduced by the quaternizing agent. This quaternizing agent is a compound of the RQ or R'Q type, in which R and R' are as defined above and Q denotes a leaving group such as a halide, a sulfate, and the like.

The cationic associative polyurethane thickener may additionally comprise a hydrophilic sequence. This sequence is provided by a fourth type of compound entering into the preparation of the polymer. This compound may be multifunctional. It is preferably difunctional. It is also possible to have a mixture where the percentage of multifunctional compound is low.

The functional groups containing a labile hydrogen are alcohol, primary or secondary amine, or thiol functional groups. This compound may be a polymer terminated at the chain ends by one of these functional groups containing a labile hydrogen.

By way of example, there may be mentioned, when polymers are not involved, ethylene glycol, diethylene glycol and propylene glycol.

In the case of a hydrophilic polymer, there may be mentioned, by way of example, polyethers, sulfonated polyesters, sulfonated polyamides, or a mixture of these polymers. Preferably, the hydrophilic compound is a polyether and in particular a polyethylene oxide or a polypropylene oxide.

The hydrophilic group noted Y in formula (A) is optional. Indeed, the units containing a quaternary or protonated amine functional group may suffice to provide the solubility or water-dispersibility necessary for this type of polymer in an aqueous solution. Although the presence of a hydrophilic group Y is optional, cationic associative polyurethane thickeners which contain such a group are nevertheless preferred.

The associative polyurethane thickener used in the present invention may also be nonionic, in particular nonionic polyurethane-polyethers. The nonionic polyurethane-polyethers may have both at least one hydrophilic moiety and at least one hydrophobic moiety. More particularly, said polymers may contain in their chain both hydrophilic sequences most often of a polyoxyethylenated nature and hydrophobic sequences which may be aliphatic linkages alone and/or cycloaliphatic and/or aromatic linkages.

Preferably, these polyether-polyurethanes comprise at least two lipophilic hydrocarbon chains, having from 6 to 30 carbon atoms, preferably from 6 to 20, separated by a hydrophilic sequence, it being possible for the hydrocarbon chains to be pendent chains or chains at the end of a hydrophilic sequence. In particular, it is possible for one or more pendent chains to be envisaged. In addition, the polymer may comprise a hydrocarbon chain at one end or at both ends of a hydrophilic sequence.

The polyether-polyurethanes may be polyblocks, in particular in triblock form. The hydrophobic sequences may be at each end of the chain (for example: triblock copolymer with hydrophilic central sequence) or distributed both at the ends and in the chain (polyblock copolymers for example). These same polymers may also be in the form of graft units or may be star shaped.

The associative polyurethane thickener can form a network in water in which the hydrophobic part connects quasi-micelles as shown in FIG. 1.

Therefore, the associative polyurethane thickeners can increase the viscosity or consistency of the composition according to the present invention. Thus, after application of the composition according to the present invention, it can recover the original elasticity of the composition quickly.

The nonionic polyether-polyurethanes containing a fatty chain may be triblock copolymers whose hydrophilic sequence is a polyoxyethylenated chain comprising from 50 to 1000 oxyethylenated groups.

The nonionic polyether-polyurethanes comprise a urethane bond between the hydrophilic sequences, hence the origin of the name.

By extension, those whose hydrophilic sequences are linked by other chemical bonds to the hydrophobic sequences are also included among the nonionic polyether-polyurethanes containing a hydrophobic chain.

By way of examples of nonionic polyether-polyurethanes containing a hydrophobic chain which can be used in the present invention, it is also possible to use Rheolate® 205 containing a urea functional group sold by the company RHEOX or else the Rheolates® 208, 204 or 212, as well as Acrysol RM 184®.

There may also be mentioned the product ELFACOS T210® containing a $C_{12}$-$C_{14}$ alkyl chain and the product ELFACOS T212® containing a Cis alkyl chain from AKZO.

The product DW 1206B® from ROHM & HAAS containing a $C_{20}$ alkyl chain and with a urethane bond, sold at 20% dry matter content in water, may also be used.

It is also possible to use solutions or dispersions of these polymers in particular in water or in an aqueous-alcoholic medium. By way of examples of such polymers, there may be mentioned Rheolate® 255, Rheolate® 278 and Rheolate® 244 sold by the company RHEOX. It is also possible to use the product DW 1206F and DW 1206J provided by the company ROHM & HAAS.

The above-described polyether-polyurethanes which can be used can also be chosen from those described in the article by G. Fonnum, J. Bakke and Fk. Hansen-Colloid Polym. Sci 271, 380-389 (1993).

As the above-described polyether-polyurethanes, mention may be made of polyurethane-polyethers comprising in their chain at least one polyoxyethylenated hydrophilic block and at least one of hydrophobic blocks containing at least one sequence chosen from aliphatic sequences, cycloaliphatic sequences, and aromatic sequences.

It is preferable that the polyurethane-polyethers comprise at least two hydrocarbon-based lipophilic chains having from 8 to 30 carbon atoms, separated by a hydrophilic block, and wherein the hydrocarbon-based chains are chosen from pendent chains and chains at the end of the hydrophilic block.

According to a specific form of the present invention, use will be made of a polyurethane/polyether that may be obtained by polycondensation of at least three compounds comprising (i) at least one polyethylene glycol comprising from 150 to 180 mol of ethylene oxide, (ii) a polyoxyethylenated stearyl alcohol comprising 100 mol of ethylene oxide, and (iii) a diisocyanate.

Such polyurethane/polyethers are sold especially by the company Elementis under the name Rheolate FX 1100® and Rheoluxe 811®, which is a polycondensate of polyethylene glycol containing 136 mol of ethylene oxide, of stearyl alcohol polyoxyethylenated with 100 mol of ethylene oxide and of hexamethylene diisocyanate (HDI) with a weight-average molecular weight of 40000 (INCI name: PEG-136/Steareth-100/HDI Copolymer).

According to another specific form of the present invention, use will be made of a polyurethane/polyether that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane/polyethers are sold in particular by the company Rohm & Haas under the names Aculyn 46® and Aculyn 44®.

Aculyn 46® having the INCI name: PEG-150/Stearyl Alcohol/SMDI Copolymer, is a polycondensate of polyethylene glycol comprising 150 or 180 mol of ethylene oxide, of stearyl alcohol and of methylenebis(4-cyclohexyl isocyanate) (SMDI) at 15% by weight in a matrix of maltodextrin (4%) and water (81%) (INCI name: PEG-150/Stearyl Alcohol/SMDI Copolymer).

Aculyn 44® (PEG-150/Decyl Alcohol/SMDI Copolymer) is a polycondensate of polyethylene glycol comprising 150 or 180 mol of ethylene oxide, of decyl alcohol and of methylenebis(4-cyclohexyl isocyanate) (SMDI) at 35% by weight in a mixture of propylene glycol (39%) and water (26%) (INCI name: PEG-150/Decyl Alcohol/SMDI Copolymer).

As the associative polyurethanes, it is preferable to use a compound represented by the following formula (1):

$$R^1—\{(O—R^2)_k—OCONH—R^3[—NHCOO—(R^4—O)_n—R^5]_h\}_m \quad (1)$$

wherein $R^1$ represents a hydrocarbon group, $R^2$ and $R^4$ independently represent alkylene groups having 2 to 4 carbon atoms, which alkylene groups may be identical or different from each other, or a phenylethylene group, $R^3$ represents a hydrocarbon group, which may optionally have a urethane bond, $R^5$ represents a branched chain or secondary hydrocarbon group, m represents a number of at least 2, h represents a number of at least 1, k represents a number within the range of 1 to 500, and n represents a number within the range of 1 to 200.

The hydrophobically modified polyurethane that is represented by the general formula (1) shown above is obtained by, for example, reacting at least one polyether polyol that is represented by the formula $R^1—[(O—R^2)_k—OH]_m$, at least one polyisocyanate that is represented by the formula $R^3—(NCO)_{h+1}$, and at least one monoalcohol that is represented by the formula $HO—(R^4—O)_n—R^5$.

In such cases, $R^1$ to $R^5$ in the general formula (1) are determined by the compounds $R^1—[(O—R^2)_k—OH]_m$, $R^3—(NCO)_{h+1}$ and $HO—(R^4—O)_n—R^5$. The loading ratios among the three compounds are not particularly limited and should preferably be such that the ratio of the isocyanate group derived from the polyisocyanate to the hydroxyl group derived from the polyether polyol and the polyether monoalcohol is selected within the range of NCO/OH of between 0.8:1 and 1.4:1.

The polyether polyol compound that is represented by the formula $R^1—[(O—R^2)_k—OH]_m$ and that may be used preferably for obtaining the associative thickener represented by the general formula (1) may be obtained from addition polymerization of an m-hydric polyol with an alkylene oxide, such as ethylene oxide, propylene oxide, butylene oxide, or epichlorohydrin, or with styrene oxide, and the like.

The polyols should preferably be di- to octa-hydric polyols. Examples of the di- to octa-hydric polyols include dihydric alcohols, such as ethylene glycol, propylene glycol, butylene glycol, hexamethylene glycol, and neopentyl glycol; trihydric alcohols, such as glycerol, trioxy isobutane, 1,2,3-butanetriol, 1,2,3-pentanetriol, 2-methyl-1,2,3-propanetriol, 2-methyl-2,3,4-butanetriol, 2-ethyl-1,2,3-butanetriol, 2,3,4-pentanetriol, 2,3,4-hexanetriol, 4-propyl-3,4,5-heptanetriol, 2,4-dimethyl-2,3,4-pentanetriol, pentamethylglycerol, pentaglycerol, 1,2,4-butanetriol, 1,2,4-pentanetriol, trimethylolethane, and trimethylolpropane; tetrahydric alcohols, such as pentaerythritol, 1,2,3,4-pentanetetrol, 2,3,4,5-hexanetetrol, 1,2,4,5-pentanetetrol, and 1,3,4,5-hexanetetrol; pentahydric alcohols, such as adonitol, arabitol, and xylitol; hexahydric alcohols, such as dipentaerythritol, sorbitol, mannitol, and iditol; and octahydric alcohols, such as sucrose.

Also, $R^2$ is determined by the alkylene oxide, styrene oxide, or the like, which is subjected to the addition. Particularly, for availability and excellent effects, an alkylene oxide having 2 to 4 carbon atoms, or styrene oxide is preferable.

The alkylene oxide, styrene oxide, or the like, to be subjected to the addition may be subjected to single polymerization, or random polymerization or block polymerization of at least two members. The procedure for the addition may be a conventional procedure. Also, the polymerization degree k may be selected within the range of 0 to 1,000, preferably within the range of 1 to 500, and more preferably within the range of 10 to 200. Further, the ratio of the ethylene group occupying $R^2$ should preferably be within the range of 50 to 100 mass % with respect to the total quantity of $R^2$. In such cases, the associative thickener appropriate for the purposes of the present invention is obtained.

Furthermore, the molecular weight of the polyether polyol compound that is represented by the formula $R^1—[(O—R^2)_k—OH]_m$ should preferably be selected within the range of 500 to 100,000, and should more preferably be selected within the range of 1,000 to 50,000.

The polyisocyanate that is represented by the formula $R^3—(NCO)_{h+1}$ and that may be used preferably for obtaining the hydrophobically modified polyether urethane represented by the general formula (1) employed in accordance with the present invention is not particularly limited in so far as the polyisocyanate has at least two isocyanate groups in the molecule. Examples of the polyisocyanates include aliphatic diisocyanates, aromatic diisocyanates, alicyclic diisocyanates, biphenyl diisocyanate, phenylmethane diisocyanate, phenylmethane triisocyanate, and phenylmethane tetraisocyanate.

Also, it is possible to employ dimers and trimers (isocyanurate bonds) of the above-enumerated polyisocyanates. Further, it is possible to employ a biuret obtained by a reaction with an amine.

Furthermore, it is possible to employ a polyisocyanate having a urethane bond obtained by a reaction of the aforesaid polyisocyanate compound and a polyol. As the polyol, di- to octa-hydric polyols are preferable, and the above-enumerated polyols are preferable. In cases where a tri- or higher-hydric polyisocyanate is used as the polyisocyanate that is represented by the formula $R^3—(NCO)_{h+1}$, it is preferable to employ the aforesaid polyisocyanate having the urethane bond.

The polyether monoalcohol that is represented by the formula $HO—(R^4—O)_n—R^5$ and that may be used preferably for obtaining the hydrophobically modified polyether urethane represented by the general formula (1) employed in accordance with the present invention is not particularly limited in so far as the polyether monoalcohol is a polyether of a straight chain, branched chain, or secondary monohydric alcohol. The polyether monoalcohol may be obtained by addition polymerization of the straight chain, branched chain, or secondary monohydric alcohol with an alkylene oxide, such as ethylene oxide, propylene oxide, butylene oxide, or epichlorohydrin, or with styrene oxide, and the like.

The compound represented by the general formula (1) may be produced by, for example, heating at a temperature of 80 to 90° C. for 1 to 3 hours and thereby causing a reaction to occur in the same manner as that in the ordinary reaction of a polyether and an isocyanate.

As the compound represented by the general formula (1), polyethyleneglycol-240/decyltetradeceth-20/hexamethylene diisocyanate copolymer is preferable. The polyethyleneglycol-240/decyltetradeceth-20/hexamethylene diisocyanate copolymer is also referred to as PEG-240/HDI copolymer bis-decyltetradeceth-20 ether.

According to the present invention, it is preferable that the associative polyurethane thickener be selected from Steareth-100/PEG-136/HDI Copolymer sold by the company Rheox under the name of Rheolate FX 1100, PEG-240/HDI Copolymer Bis-decyltetradeceth-20 ether sold by the company Asahi Denka under the name of Adekanol GT-700, and mixtures thereof.

(ii) Among the crosslinked acrylic acid homopolymers that may be mentioned are those crosslinked with an allylic alcohol ether of the sugar series. Mention may be made of carbomer, which is a homopolymer of acrylic acid crosslinked with an allyl ether of pentaerythritol, an allyl ether of sucrose, or an allyl ether of propylene, such as the products sold under the names Carbopol 980, 981, 954, 2984, and 5984 by the company Lubrizol or the products sold under the names Synthalen M and Synthalen K by the company 3 VSA.

(iii) The crosslinked copolymers of (meth)acrylic acid and of $C_1$-$C_6$ alkyl acrylate can be chosen from crosslinked copolymers of methacrylic acid and of ethyl acrylate as an aqueous dispersion comprising 38% active material sold, for example, under the name Viscoatex 538C by the company Coatex, and crosslinked copolymers of acrylic acid and of ethyl acrylate as an aqueous dispersion comprising 28% active material sold under the name Aculyn 33 by the company Rohm & Haas. Crosslinked copolymers of methacrylic acid and of ethyl acrylate include an aqueous dispersion comprising 30% active material sold under the name CARBOPOL AQUA SF-1 by the company NOVEON.

(iv) Among the nonionic homopolymers or copolymers comprising ethylenically unsaturated monomers of ester and/or amide type, mention may be made of the products sold under the names: Cyanamer P250 by the company Cytec (polyacrylamide); PMMA MBX-8C by the company US Cosmetics (methyl methacrylate/ethylene glycol dimethacrylate copolymer); Acryloid B66 by the company Rohm & Haas (butyl methacrylate/methyl methacrylate copolymer); and BPA 500 by the company Kobo (polymethyl methacrylate).

(v) Ammonium acrylate homopolymers that may be mentioned include the product sold under the name Microsap PAS 5193 by the company Hoechst.

Copolymers of ammonium acrylate and of acrylamide include the product sold under the name Bozepol C Nouveau or the product PAS 5193 sold by the company Hoechst (which are described and prepared in documents FR-2 416 723, U.S. Pat. Nos. 2,798,053, and 2,923,692).

(vi) The polysaccharides are, for example, chosen from glucans, modified and unmodified starches (such as those derived, for example, from cereals, for instance wheat, corn, or rice, from vegetables, for instance yellow peas, and tubers, for instance potatoes or cassava), amylose, amylopectin, glycogen, dextrans, celluloses, and derivatives thereof (e.g., methylcelluloses, hydroxyalkylcelluloses, hydroxyethylcelluloses, and carboxymethylcelluloses), mannans, xylans, lignins, arabans, galactans, galacturonans, chitins, chitosans, glucuronoxylans, arabinoxylans, xyloglucans, glucomannans, pectic acids, and pectins, alginic acid and alginates, arabinogalactans, carrageenans, agars, glycosaminoglucans, gum arabics, gum tragacanths, ghatti gums, karaya gums, carob gums, galactomannans, such as guar gums, and nonionic derivatives thereof (e.g., hydroxypropyl guar), *sclerotium* gum and xanthan gums, and mixtures thereof.

For example, the polysaccharides that may be used are chosen from those described, for example, in "Encyclopedia of Chemical Technology", Kirk-Othmer, Third Edition, 1982, Volume 3, pp. 896-900, and Volume 15, pp. 439-458, in "Polymers in Nature" by E. A. MacGregor and C. T. Greenwood, published by John Wiley & Sons, Chapter 6, pp. 240-328, 1980, and in "Industrial Gums-Polysaccharides and their Derivatives", edited by Roy L. Whistler, Second Edition, published by Academic Press Inc., the content of these three publications being entirely incorporated by reference.

For example, starches, guar gums, celluloses, and derivatives thereof can be used.

Among the starches that may be used, mention may be made, for example, of macromolecules in the form of polymers comprising base units which are anhydroglucose units. The number of these units and their assembly make it possible to distinguish between amylose (linear polymer) and amylopectin (branched polymer). The relative proportions of amylose and amylopectin, as well as their degree of polymerization, can vary according to the botanical origin of the starches.

The molecules of starches used may have cereals or tubers as their botanical origin. Thus, the starches can be, for example, chosen from maize, rice, cassava, tapioca, barley, potato, wheat, sorghum, and pea starches.

Starches generally exist in the form of a white powder, insoluble in cold water, whose elementary particle size ranges from 3 to 100 microns.

The starches may be optionally $C_1$-$C_6$ hydroxyalkylated or $C_1$-$C_6$ acylated (such as acetylated). The starches may have also undergone heat treatments.

Distarch phosphates or compounds rich in distarch phosphate, such as the product provided under the references PREJEL VA-70-T AGGL (gelatinized hydroxypropylated cassava distarch phosphate) or PREJEL TK1 (gelatinized cassava distarch phosphate) or PREJEL 200 (gelatinized acetylated cassava distarch phosphate) by the company AVEBE, may also be used.

The guar gums can be modified or unmodified.

The unmodified guar gums are, for example, the products sold under the name Vidogum GH 175 by the company Unipectine and under the names Meypro-Guar 50 and Jaguar C by the company Meyhall.

The modified nonionic guar gums are, for example, modified with $C_1$-$C_6$ hydroxyalkyl groups.

Among the hydroxyalkyl groups that may be mentioned, for example, are hydroxymethyl, hydroxyethyl, hydroxypropyl, and hydroxybutyl groups.

These guar gums are well known in the prior art and can be prepared, for example, by reacting the corresponding alkene oxides such as propylene oxides, with the guar gum so as to obtain a guar gum modified with hydroxypropyl groups.

The degree of hydroxyalkylation, which corresponds to the number of alkylene oxide molecules consumed by the number of free hydroxyl functions present on the guar gum, may, for example, range from 0.4 to 1.2.

Such nonionic guar gums optionally modified with hydroxyalkyl groups are sold, for example, under the trade names Jaguar HP8, Jaguar HP60, Jaguar HP120, Jaguar DC 293, and Jaguar HP 105 by the company Rhodia Chimie (Meyhall) or under the name Galactasol $4H_{4FD2}$ by the company Aqualon.

Among the celluloses and cellulose derivatives, such as cellulose modified with hydroxylalkyl groups, that are used are, for example, hydroxypropylmethylcellulose, hydroxyethylcellulose, and hydroxypropylcellulose, as well as hydrophobicized hydroxypropylmethylcellulose. Mention may be made of the products sold under the names Klucel E F, Klucel H, Klucel L H F, Klucel M F, and Klucel G by the company Aqualon.

(vii) The fatty alcohols are, for example, chosen from myristyl alcohol, cetyl alcohol, stearyl alcohol, and behenyl alcohol.

It is preferable that the thickening agent be selected from hydrophilic thickeners. The hydrophilic thickeners can thicken an aqueous phase formed by the (e) water in the composition according to the present invention.

It is more preferable that the thickening agent be selected from polysaccharides, more preferably cellulose derivatives, and even more preferably hydroxyalkyl celluloses such as hydroxyethylcelulose.

The amount of the thickening agent(s) in the composition according to the present invention may be 0.01% by weight or more, preferably 0.05% by weight or more, and more preferably 0.1% by weight or more, relative to the total weight of the composition.

The amount of the thickening agent(s) in the composition according to the present invention may be 5% by weight or less, preferably 1% by weight or less, and more preferably 0.5% by weight or less, relative to the total weight of the composition.

The amount of the thickening agent(s) in the composition according to the present invention may be from 0.01% to 5% by weight, preferably from 0.05% to 1% by weight, and more preferably from 0.1% to 0.5% by weight, relative to the total weight of the composition.

(Other Ingredients)

The composition according to the present invention may also include at least one optional or additional ingredient.

The amount of the optional or additional ingredient(s) is not limited, but may be from 0.01% to 30% by weight, preferably from 0.1% to 20% by weight, and more preferably from 1% to 10% by weight, relative to the total weight of the composition according to the present invention.

The optional or additional ingredient(s) may be selected from the group consisting of cationic, anionic or amphoteric surfactants; UV filters; peptides and derivatives thereof; protein hydrolyzates; swelling agents and penetrating agents; agents for combating hair loss; anti-dandruff agents; suspending agents; sequestering agents; opacifying agents; vitamins or provitamins; fragrances; preserving agents, stabilizers; and mixtures thereof.

The aqueous phase of the composition according to the present invention may include, in addition to water, one or several cosmetically acceptable organic solvents, which may be alcohols: in particular monovalent alcohols such as ethyl alcohol, isopropyl alcohol, benzyl alcohol and phenylethyl alcohol; sugars; sugar alcohols; and ethers such as ethylene glycol monomethyl, monoethyl and monobutyl ethers, propylene glycol monomethyl, monoethyl and monobutyl ether, and butylene glycol monomethyl, monoethyl and monobutyl ethers.

The organic solvent(s) may then be present in a concentration of from 0.01% to 30% by weight, preferably from 0.1% to 20% by weight, and more preferably from 1% to 15% by weight, relative to the total weight of the composition.

(Preparation)

The composition according to the present invention can be prepared by mixing the above-described essential and optional ingredients in a conventional manner.

For example, the composition according to the present invention can be prepared by a process comprising the step of mixing (a) at least one inorganic compound selected from silicic acids and salts thereof;

(b) at least one organic compound selected from amino acids, derivatives thereof, and salts thereof;

(c) at least one alkaline agent other than the (a) inorganic compound and the (b) organic compound;

(d) at least one fatty material; and (e) water, and optionally (f) at least one dye.

For the above ingredients (a) to (f), those explained above can be used.

It is possible to further mix therein any of the optional ingredients.

[Use]

The composition according to the present invention is preferably used for cosmetic purposes of keratin fibers. Thus, the composition according to the present invention is preferably a cosmetic composition for keratin fibers, in particular for bleaching or coloring keratin fibers.

As the keratin fibers, mention may be made of hair, eyebrows and eyelashes.

If the composition according to the present invention explained above is used for bleaching keratin fibers such as hair, for example, the composition according to the present invention which includes no dye can be used as a mixture with another composition comprising (g) at least one oxidizing agent explained below.

Alternatively, if the composition according to the present invention is used for dyeing keratin fibers such as hair, the composition according to the present invention which further includes (f) at least one dye can be used as a mixture with another composition comprising (g) at least one oxidizing agent.

The above composition including the (g) at least one oxidizing agent can function as a developer.

The above mixture may be regarded as a ready-to-use composition. For the purposes of the present invention, the expression "ready-to-use composition" is defined herein as a composition to be applied immediately to keratin fibers such as hair. The ready-to-use composition can also be a cosmetic composition for keratin fibers, in particular for bleaching or coloring keratin fibers, such as hair.

The mixing ratio of the composition according to the present invention and another composition is not limited. The mixing ratio may be 1:3 to 3:1, preferably 1:2 to 2:1, and more preferably 1:1, as the weight ratio thereof.

(Oxidizing Agent)

The developer which can be combined with the composition according to the present invention includes at least one (g) oxidizing agent. If two or more (g) oxidizing agents are used, they may be the same or different.

The (g) oxidizing agent may be chosen from hydrogen peroxide, peroxygenated salts, and compounds capable of producing hydrogen peroxide by hydrolysis. For example, the (g) oxidizing agent can be chosen from hydrogen peroxide, urea peroxide, alkali metal bromates and ferricyanides and persalts such as perborates and persulphates. At least one oxidase enzyme chosen, for example, from laccases, peroxidases and 2-electron oxidoreductases such as uricase may also be used as the (g) oxidizing agent, where appropriate in the presence of the respective donor or co-factor thereof.

In one embodiment, the (g) oxidizing agent is hydrogen peroxide, and the developer is an aqueous hydrogen peroxide solution.

In one embodiment, when the developer is an aqueous hydrogen peroxide solution, the developer may comprise at least one hydrogen peroxide stabilizer, which may be chosen, for example, from alkali metal and alkaline-earth metal pyrophosphates, alkali metal and alkaline-earth metal stannates, phenacetin and salts of acids and of oxyquinoline, for example, oxyquinoline sulphate. In another embodiment, at least one stannate optionally in combination with at least one pyrophosphate is used.

It is also possible to use salicylic acid and its salts, pyridinedicarboxylic acid and its salts, and paracetamol.

In the developer in the form of an aqueous hydrogen peroxide solution, the concentration of the hydrogen peroxide stabilizer may range from 0.0001% to 5% by weight such as from 0.01% to 2% by weight, relative to the total weight of the developer.

In the developer in the form of an aqueous hydrogen peroxide solution, the concentration ratio of the hydrogen peroxide to the possible at least one stabilizer may range from 0.05:1 to 1,000:1, such as from 0.1:1 to 500:1 and further such as from 1:1 to 200:1.

The amount of the (g) oxidizing agent(s) in the developer may be from 0.1% by weight or more, preferably 0.5% by weight or more, and more preferably from 1% by weight or more, relative to the total weight of the composition.

The amount of the (g) oxidizing agent(s) in the developer may be from 20% by weight or less, preferably from 15% by weight or less, and more preferably from 10% by weight or less, relative to the total weight of the composition.

The amount of the (g) oxidizing agent(s) in the developer may be from 0.1% to 20% by weight, preferably from 0.5% to 15% by weight, and more preferably from 1% to 10% by weight, relative to the total weight of the composition.

[Kit]

The present invention also relates to a kit for keratin fibers, preferably a cosmetic kit, and more preferably a cosmetic kit for bleaching or dyeing keratin fibers, in particular hair, comprising:

a first compartment comprising a first composition comprising (a) at least one inorganic compound selected from silicic acids and salts thereof;

(b) at least one organic compound selected from amino acids, derivatives thereof, and salts thereof;

(c) at least one alkaline agent other than the (a) inorganic compound and the (b) organic compound;

(d) at least one fatty material;

(e) water, and optionally (f) at least one dye, and a second compartment comprising a second composition comprising (g) at least one oxidizing agent.

For the above ingredients (a) to (f), those explained above can be used.

It is possible to use the kit by, for example, dispensing or discharging the first composition from the first compartment, while dispensing or discharging the second composition from the second compartment, followed by treating keratin fibers such as hair with the mixture of the first and second compositions.

The mixture of the first and second compositions may be regarded as the ready-to-use composition as explained above.

The mixing ratio of the first and second compositions is not limited. The mixing ratio may be 1:3 to 3:1, preferably 1:2 to 2:1, and more preferably 1:1, as the weight ratio thereof.

[Process]

The present invention also relates to a process, preferably a cosmetic process, and more preferably a cosmetic process for bleaching or dyeing keratin fibers, in particular hair, comprising the steps of:

(1) mixing a first composition and a second composition to prepare a mixture, wherein the first composition comprises (a) at least one inorganic compound selected from silicic acids and salts thereof, (b) at least one organic compound selected from amino acids, derivatives thereof, and salts thereof, (c) at least one alkaline agent other than the (a) inorganic compound and the (b) organic compound, (d) at least one fatty material, (e) water, and optionally (f) at least one dye, and the second composition comprises (g) at least one oxidizing agent; and (2) applying the mixture to the keratin fibers.

For the above ingredients (a) to (f), those explained above can be used.

The mixture of the first and second compositions may be regarded as the ready-to-use composition as explained above.

The mixing ratio of the first and second compositions is not limited. The mixing ratio may be 1:3 to 3:1, preferably 1:2 to 2:1, and more preferably 1:1, as the weight ratio thereof.

It is preferable that the process according to the present invention further comprise a step of washing, with or without drying, keratin fibers before and/or after the step of applying the mixture of the first and second compositions, as a ready-to-use composition, onto the keratin fibers.

The step of applying the ready-to-use composition onto the keratin fibers can be performed by a conventional applicator such as a brush, or even by the hands.

The keratin fibers to which the ready-to-use composition has been applied can be left for an appropriate time which is required to treat the keratin fibers. The time length for the treatment is not limited, but it may be from 1 minute to 1 hour, preferably 1 minute to 30 minutes, and more preferably 1 minute to 15 minutes. For example, the time for dyeing the keratin fibers may be from 1 to 20 minutes, preferably 5 to 15 minutes.

The keratin fibers may be treated at room temperature. Alternatively, the keratin fibers can be heated at 25° C. to 65° C., preferably 30° C. to 60° C., more preferably 35° C. to 55° C., and even more preferably 40° C. to 50° C., before and/or during and/or after the step of applying the ready-to-use composition onto the keratin fibers.

EXAMPLES

The present invention will be described in a more detailed manner by way of examples. However, these examples should not be construed as limiting the scope of the present invention. The examples below are presented as non-limiting illustrations in the field of the present invention.

Example 1 and Comparative Examples 1-3

The following compositions according to Example 1 and Comparative Examples 1-3, shown in Table 1, were prepared by mixing the ingredients shown in Table 1. The numerical values for the amounts of the ingredients shown in Table 1 are all based on "% by weight" as raw materials.

TABLE 1

| | Ex. 1 | Comp. Ex. 1 | Comp. Ex. 2 | Comp. Ex. 3 |
|---|---|---|---|---|
| Mineral Oil | 58 | 58 | 58 | 58 |
| Steareth-2 | 2 | 2 | 2 | 2 |
| Decyl Glucoside (ca. 53%) | 2.2 | 2.2 | 2.2 | 2.2 |
| Hydroxyethylcellulose | 0.25 | 0.25 | 0.25 | 0.25 |
| Polyquaternium-10 | 0.5 | 0.5 | 0.5 | 0.5 |
| Titanium Dioxide | 0.3 | 0.3 | 0.3 | 0.3 |
| Ascorbic Acid | 0.12 | 0.12 | 0.12 | 0.12 |
| Sodium Metabisulfite | 0.22 | 0.22 | 0.22 | 0.22 |
| EDTA | 0.2 | 0.2 | 0.2 | 0.2 |
| Ethanolamine | 5.35 | 5.35 | 5.35 | 5.35 |
| Sodium Metasilicate | 1 | 1 | — | — |
| Glycine | 1.5 | — | 1.5 | — |
| Water | qsp. 100 | qsp. 100 | qsp. 100 | qsp. 100 |
| Bleach Test | A | B | C | C |
| Labile Protein Test | A | D | A | C |
| Cysteic Acid Test | A | D | A | A |

[Evaluations]

(Bleach Test)

Each of the compositions according to Example 1 and Comparative Examples 1-3 was mixed with the developer of the formulation shown in Table 2 below. The mixing weight ratio of the composition and the developer was 1 to 1.

TABLE 2

| | wt % |
|---|---|
| Cetearyl Alcohol | 6 |
| Steareth-20 | 5 |
| Mineral Oil | 25 |
| PEG-4 Rapeseedamide | 1.3 |
| Tocopherol | 0.1 |
| Glycerin | 0.5 |
| Hexadimethrine Chloride (ca. 60%) | 0.25 |
| Tetrasodium Pyrophosphate | 0.04 |
| Hydrogen Peroxide (ca. 50%) | 18 |
| Tetrasodium Etidronate (ca. 30%) | 0.2 |
| Sodium Salicylate | 0.035 |
| Polyquaternium-6 (ca. 40%) | 0.5 |
| Phosphoric Acid | qs. pH 2.2 |
| Water | qsp. 100 |

3 g of the mixture thus obtained was applied on 1 g of a tress of natural Chinese natural black hair for 35 minutes at 27° C., followed by washing with water, shampooing, rinsing once and drying the tress.

The difference in color of the tress before and after the above bleaching process was evaluated by using Minolta CM-3600A. ΔE* was calculated by the following formula (1), based on CIE1976.

$$\Delta E^*_i=\{(L_i-L_0)^2+(a_i-a_0)^2+(b_i-b_0)^2\}^{1/2} \quad (1)$$

In the formula (1), ($L_i$, $a_i$, $b_i$) refer to the (L*, a*, b*) values of the hair tress after bleaching, and ($L_0$, $a_0$, $b_0$) refer to the (L*, a*, b*) values of the hair tress before bleaching.

ΔE* values were scored in accordance with the following criteria. The larger ΔE* is, the more bleaching there is.

A: >20
B: 19-20
C: 18-19
D: <18

The results are shown in Table 1.

(Labile Protein Test)

Each of the compositions according to Example 1 and Comparative Examples 1-3 was mixed with a developer (iNoa 30 Volume Developer: commercial product from L'Oreal). The mixing weight ratio of the composition and the developer was 1 to 1.

3 g of the mixture thus obtained was applied on 1 g of a tress of natural Chinese natural black hair for 50 minutes at 33° C., followed by washing with water, shampooing, rinsing once and drying the tress. The process was repeated four times.

Each tress was treated with TRIZMA-Base/mercaptoethanol mixture to obtain an extract, and the extract was hydrolyzed with 9N hydrochloric acid. Labile protein was measured with Hitachi L8500 amino acid auto-analyzer.

Labile protein amounts (g/100 g of hair) were scored in accordance with the following criteria. The larger the labile protein amount is, the higher the damage is.

A: <6
B: 6-7
C: 7-8
D: >8

The results are shown in Table 1.

(Cysteic Acid Test)

Each of the compositions according to Example 1 and Comparative Examples 1-3 was mixed with the developer (iNoa 30 volume: L'Oreal commercial product). The mixing weight ratio of the composition and the developer was 1 to 1.

3 g of the mixture thus obtained was applied on 1 g of a tress of natural Chinese natural black hair for 50 minutes at 33° C., followed by washing with water, shampooing, rinsing once and drying the tress. The process was repeated four times.

Each tress was hydrolyzed with methanesulfonic acid and 6N hydrochloric acid. The amount of cysteic acid in the hydrolyzate was measured with Hitachi L8500 amino acid auto-analyzer.

Cysteic acid amounts (g/100 g of hair) were scored in accordance with the following criteria. The larger the cysteic acid amount is, the higher the damage is.

A: <8
B: 8-9
C: 9-10
D: >10

The results are shown in Table 1.

The composition according to Example 1 shows better results with regard to bleaching as well as reduced hair damage reflected by the lower scores regarding the labile protein and cysteic acid than those according to Comparative Examples 1 to 3.

Examples 2-4 and Comparative Example 4

The following compositions according to Examples 2-4 and Comparative Example 4, shown in Table 3 were prepared by mixing the ingredients shown in Table 3. The numerical values for the amounts of the ingredients shown in Table 3 are all based on "% by weight" as raw materials.

TABLE 3

| | Ex. 2 | Ex. 3 | Ex. 4 | Comp. Ex. 4 |
|---|---|---|---|---|
| Mineral Oil | 58 | 50 | 40 | — |
| Steareth-2 | 2 | 2 | 2 | 2 |
| Decyl Glucoside (ca. 53%) | 2.2 | 2.2 | 2.2 | 2.2 |
| Hydroxyethylcellulose | 0.25 | 0.25 | 0.25 | 0.25 |
| Polyquaternium-10 | 0.5 | 0.5 | 0.5 | 0.5 |
| Titanium Dioxide | 0.3 | 0.3 | 0.3 | 0.3 |
| Ascorbic Acid | 0.12 | 0.12 | 0.12 | 0.12 |
| Sodium Metabisulfite | 0.22 | 0.22 | 0.22 | 0.22 |
| EDTA | 0.2 | 0.2 | 0.2 | 0.2 |
| Ethanolamine | 5.35 | 5.35 | 5.35 | 5.35 |
| Sodium Metasilicate | 1 | 1 | 1 | 1 |
| Glycine | 1.5 | 1.5 | 1.5 | 1.5 |
| Water | qsp. 100 | qsp. 100 | qsp. 100 | qsp. 100 |
| L* | 25.9 | 26.7 | 26.4 | 28.1 |
| a* | 8.0 | 8.5 | 8.7 | 9.4 |
| b* | 10.5 | 11.5 | 11.6 | 13.7 |
| ΔE* | 17.6 | 17.3 | 15.5 | 13.5 |

Each of the compositions according to Examples 2-4 and Comparative Example 4 was mixed with the developer with the formulation shown in Table 2 above. The mixing weight ratio of the composition and the developer was 1 to 1.

3 g of the mixture thus obtained was applied on 1 g of a tress of natural Chinese natural black hair for 35 minutes at 27° C., followed by washing with water, shampooing, rinsing once and drying the tress.

The difference in color of the tress before and after the above bleaching process was evaluated by using Minolta CM-3600A. ΔE* was calculated by the following formula (1), based on CIE1976.

$$\Delta E^*_i=\{(L_i-L_0)^2+(a_i-a_0)^2+(b_i-b_0)^2\}^{1/2} \quad (1)$$

In the formula (1), ($L_i$, $a_i$, $b_i$) refer to the (L*, a*, b*) values of the hair tress after bleaching, and ($L_0$, $a_0$, $b_0$) refer to the (L*, a*, b*) values of the hair tress before bleaching.

The results are shown in Table 3. The larger ΔE* is, the more bleaching there is.

It was found that the use of a fatty material contributed to higher bleaching effects than non-use of the fatty material. Furthermore, the use of 40% by weight or more, and preferably 50% by weight or more, of a fatty material provided clearly higher bleaching effects than non-use of the fatty material.

Example 5

The following composition according to Example 5, shown in Table 4, was prepared by mixing the ingredients shown in Table 4. The numerical values for the amounts of the ingredients shown in Table 4 are all based on "% by weight" as raw materials.

TABLE 4

| | Ex. 5 |
|---|---|
| Mineral Oil | 58 |
| Steareth-2 | 2 |
| Decyl Glucoside (ca. 53%) | 2.2 |
| Hydroxyethylcellulose | 0.25 |
| Polyquaternium-10 | 0.5 |
| Titanium Dioxide | 0.3 |
| Ascorbic Acid | 0.12 |
| Sodium Metabisulfite | 0.22 |
| EDTA | 0.2 |
| Ethanolamine | 5.35 |
| Sodium Metasilicate | 1 |
| Glycine | 1.5 |
| Toluene-2,5-Diamine | 0.192 |
| 4-Amino-2-Hydroxytoluene | 0.92 |
| 5-Amino-6-Chloro-o-Cresol | 0.2 |
| 1-Hydroxyethyl-4,5-Diamino Pyrazole Sulfate | 1.12 |
| p-Aminophenol | 0.128 |
| Water | qsp. 100 |

The composition according to Example 5 was mixed with the developer with the formulation shown in Table 2 above. The mixing weight ratio of the composition and the developer was 1 to 1.

3 g of the mixture thus obtained was applied on 1 g of each of a tress of natural Chinese natural black hair, a Chinese bleached hair, and a Goatee tress, for 35 minutes at 27° C., followed by washing with water, shampooing, rinsing once and drying the tress.

It was found that the composition according to Example 5 provided sufficient coloring effects for all of the three tested tresses.

The invention claimed is:

1. A composition for treating keratin fibers, comprising:

(a) sodium metasilicate;

(b) glycine;

(c) at least one alkaline agent chosen from alkanolamines;

(d) mineral oil; and (e) water, wherein the amount of (a) sodium metasilicate in the composition is from 0.05% to 10% by weight, relative to the total weight of the composition, the amount of (b) glycine in the composition is from 0.1% to 10% by weight, relative to the total weight of the composition, the amount of (c) at least one alkaline agent in the composition is from 0.1% to 20% by weight, relative to the total weight of the composition, the amount of (d) mineral oil in the composition is at least 40% by weight, relative to the total weight of the composition, and the amount of (e) water in the composition ranges from 10% to 40% by weight, relative to the total weight of the composition.

2. The composition according to claim 1, wherein the amount of the (a) sodium metasilicate in the composition ranges from 0.1% to 5% by weight, relative to the total weight of the composition.

3. The composition according to claim 1, wherein the amount of the (b) glycine in the composition ranges from 0.5% to 5% by weight, relative to the total weight of the composition.

4. The composition according to claim 1, wherein the (c) at least one alkaline agent is chosen from monoethanolamine, diethanolamine, triethanolamine, monois propanolamine, diisopropanolamine, N-dimethylethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris (hydroxymethylamino) methane, or mixtures of two or more thereof.

5. The composition according to claim 1, wherein the amount of the (c) at least one alkaline agent in the composition ranges from 0.5% to 15% by weight, relative to the total weight of the composition.

6. The composition according to claim 1, wherein the amount of the (d) mineral oil in the composition ranges from 45% by weight or more, relative to the total weight of the composition.

7. The composition according to claim 1, wherein the amount of the (e) water in the composition ranges from 15% to 35% by weight, relative to the total weight of the composition.

8. The composition according to claim 1, further comprising: (f) at least one dye.

9. A method for treating keratin fibers, comprising:

(1) mixing a first composition and a second composition to prepare a mixture, wherein the first composition comprises:

(a) sodium metasilicate, (b) glycine, (c) at least one alkaline agent chosen from alkanolamines, (d) mineral oil, (e) water, and (f) optionally, at least one dye, wherein the amount of (a) sodium metasilicate in the first composition is from 0.05% to 10% by weight, relative to the total weight of the first composition, the amount of (b) glycine in the first composition is from 0.1% to 10% by weight, relative to the total weight of the first composition, the amount of (c) at least one alkaline agent in the first composition is from 0.1% to 20% by weight, relative to the total weight of the first composition, the amount of (d) mineral oil in the first composition is at least 40% by weight, relative to the total weight of the first composition, and the amount of (e) water in the first composition ranges from 10% to 40% by weight, relative to the total weight of the first composition, and wherein the second composition comprises:

(g) at least one oxidizing agent; and (2) applying the mixture to the keratin fibers.

* * * * *